(12) United States Patent  (10) Patent No.: US 7,610,092 B2
Cowan et al. (45) Date of Patent: *Oct. 27, 2009

(54) LEADLESS TISSUE STIMULATION SYSTEMS AND METHODS

(75) Inventors: Mark W. Cowan, Fremont, CA (US);
Debra S. Echt, Woodside, CA (US);
Richard E. Riley, Palo Alto, CA (US);
Axel F. Brisken, Fremont, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 483 days.

This patent is subject to a terminal disclaimer.

(21) Appl. No.: 11/315,023

(22) Filed: Dec. 21, 2005

(65) Prior Publication Data

US 2006/0136004 A1    Jun. 22, 2006

Related U.S. Application Data

(60) Provisional application No. 60/689,606, filed on Jun. 9, 2005, provisional application No. 60/639,027, filed on Dec. 21, 2004, provisional application No. 60/639,037, filed on Dec. 21, 2004.

(51) Int. Cl.
*A61N 1/372* (2006.01)
(52) U.S. Cl. ............................................ 607/33; 607/9
(58) Field of Classification Search ................... 607/33, 607/9
See application file for complete search history.

(56) References Cited

U.S. PATENT DOCUMENTS 3,659,615 A    5/1972   Enger 3,693,627 A    9/1972   Berkovits (Continued)

FOREIGN PATENT DOCUMENTS

DE           4330680        3/2005

(Continued)

OTHER PUBLICATIONS

International Search Report and Written Opinion of PCT Application No. PCT/US2007/076812, mailed Apr. 7, 2008, 8 pages total.

(Continued)

*Primary Examiner*—Mark W Bockelman
*Assistant Examiner*—Eric D Bertram
(74) *Attorney, Agent, or Firm*—Townsend and Townsend and Crew LLP

(57) ABSTRACT

Systems including an implantable receiver-stimulator and an implantable controller-transmitter are used for leadless electrical stimulation of body tissues. Cardiac pacing and arrhythmia control is accomplished with one or more implantable receiver-stimulators and an external or implantable controller-transmitter. Systems are implanted by testing external or implantable devices at different tissue sites, observing physiologic and device responses, and selecting sites with preferred performance for implanting the systems. In these systems, a controller-transmitter is activated at a remote tissue location to transmit/deliver acoustic energy through the body to a receiver-stimulator at a target tissue location. The receiver-stimulator converts the acoustic energy to electrical energy for electrical stimulation of the body tissue. The tissue locations(s) can be optimized by moving either or both of the controller-transmitter and the receiver-stimulator to determine the best patient and device responses.

17 Claims, 10 Drawing Sheets

U.S. PATENT DOCUMENTS

| | | | |
|---|---|---|---|
| 3,698,398 | A | 10/1972 | Berkovits |
| 3,735,756 | A | 5/1973 | Richards et al. |
| 3,832,994 | A | 9/1974 | Bicher et al. |
| 3,857,382 | A | 12/1974 | Williams et al. |
| 3,939,844 | A | 2/1976 | Peuignot |
| 3,942,534 | A | 3/1976 | Allen et al. |
| 4,181,133 | A | 1/1980 | Kolenik et al. |
| 4,256,115 | A | 3/1981 | Bilitch |
| 4,265,228 | A | 5/1981 | Zoll |
| 4,280,502 | A | 7/1981 | Baker, Jr. et al. |
| 4,561,442 | A | 12/1985 | Vollmann et al. |
| 4,577,633 | A | 3/1986 | Berkovits et al. |
| 4,651,716 | A | 3/1987 | Forester et al. |
| 4,690,144 | A | 9/1987 | Rise et al. |
| 4,830,006 | A | 5/1989 | Haluska et al. |
| 5,018,523 | A | 5/1991 | Bach, Jr. et al. |
| 5,063,928 | A | 11/1991 | Grevis |
| 5,103,129 | A | 4/1992 | Slayton et al. |
| 5,113,859 | A | 5/1992 | Funke |
| 5,165,403 | A | 11/1992 | Mehra |
| 5,170,784 | A | 12/1992 | Ramon |
| 5,174,289 | A | 12/1992 | Cohen |
| 5,193,539 | A | 3/1993 | Schulman et al. |
| 5,292,338 | A | 3/1994 | Bardy |
| 5,377,166 | A | 12/1994 | Kuhn |
| 5,405,367 | A | 4/1995 | Schulman et al. |
| 5,411,535 | A | 5/1995 | Fujii et al. |
| 5,433,731 | A | 7/1995 | Hoegnelid et al. |
| 5,674,251 | A | 10/1997 | Combs et al. |
| 5,749,909 | A | 5/1998 | Schroeppel et al. |
| 5,751,539 | A | 5/1998 | Stevenson et al. |
| 5,757,104 | A | 5/1998 | Getman et al. |
| 5,766,227 | A | 6/1998 | Nappholz et al. |
| 5,800,464 | A | 9/1998 | Kieval |
| 5,814,089 | A | 9/1998 | Stokes et al. |
| 5,817,130 | A | 10/1998 | Cox et al. |
| 5,844,349 | A | 12/1998 | Oakley et al. |
| 5,871,506 | A | 2/1999 | Mower |
| 5,935,158 | A | 8/1999 | Holmstrom et al. |
| 5,978,204 | A | 11/1999 | Stevenson |
| 5,998,910 | A | 12/1999 | Park et al. |
| 6,037,704 | A | 3/2000 | Welle |
| 6,070,101 | A | 5/2000 | Struble et al. |
| 6,078,837 | A | 6/2000 | Peterson et al. |
| 6,110,098 | A | 8/2000 | Renirie et al. |
| 6,223,079 | B1 | 4/2001 | Bakels et al. |
| 6,233,484 | B1 | 5/2001 | Ben-Haim et al. |
| 6,330,475 | B1 | 12/2001 | Renirie et al. |
| 6,366,816 | B1 | 4/2002 | Marchesi |
| 6,408,205 | B1 | 6/2002 | Renirie et al. |
| 6,424,234 | B1 | 7/2002 | Stevenson |
| 6,439,236 | B1 | 8/2002 | Porter et al. |
| 6,445,953 | B1 | 9/2002 | Bulkes et al. |
| 6,527,729 | B1 | 3/2003 | Turcott |
| 6,534,895 | B2 | 3/2003 | Kadota et al. |
| RE38,119 | E | 5/2003 | Mower |
| 6,628,989 | B1 | 9/2003 | Penner et al. |
| 6,645,145 | B1 | 11/2003 | Dreschel et al. |
| 6,647,292 | B1 | 11/2003 | Bardy et al. |
| 6,654,638 | B1 | 11/2003 | Sweeney |
| 6,671,547 | B2 | 12/2003 | Lyster et al. |
| 6,707,230 | B2 | 3/2004 | Smith et al. |
| 6,721,597 | B1 | 4/2004 | Bardy et al. |
| 6,728,576 | B2 | 4/2004 | Thompson et al. |
| 6,754,528 | B2 | 6/2004 | Bardy et al. |
| 6,754,531 | B1 | 6/2004 | Kroll et al. |
| 6,764,446 | B2 | 7/2004 | Wolinsky et al. |
| 6,788,974 | B2 | 9/2004 | Bardy et al. |
| 6,834,204 | B2 | 12/2004 | Ostroff et al. |
| 6,856,835 | B2 | 2/2005 | Bardy et al. |
| 6,970,742 | B2 | 11/2005 | Mann et al. |
| 7,043,292 | B2 | 5/2006 | Tarjan et al. |
| 7,200,437 | B1 * | 4/2007 | Nabutovsky et al. ............ 607/9 |
| 7,283,874 | B2 | 10/2007 | Penner |
| 7,349,740 | B2 | 3/2008 | Soykan et al. |
| 2002/0077673 | A1 | 6/2002 | Penner et al. |
| 2003/0013974 | A1 | 1/2003 | Natarajan et al. |
| 2003/0069625 | A1 | 4/2003 | Ley et al. |
| 2004/0015104 | A1 | 1/2004 | Goldberger |
| 2004/0167580 | A1 | 8/2004 | Mann et al. |
| 2004/0172083 | A1 * | 9/2004 | Penner ........................ 607/35 |
| 2004/0204744 | A1 | 10/2004 | Penner et al. |
| 2004/0260346 | A1 | 12/2004 | Overall et al. |
| 2006/0009831 | A1 | 1/2006 | Lau et al. |
| 2006/0224067 | A1 | 10/2006 | Giftakis et al. |
| 2006/0241701 | A1 | 10/2006 | Markowitz et al. |
| 2007/0032749 | A1 | 2/2007 | Overall et al. |
| 2007/0232936 | A1 | 10/2007 | Mann et al. |
| 2007/0260286 | A1 | 11/2007 | Giftakis et al. |
| 2007/0265677 | A1 | 11/2007 | Giftakis et al. |

FOREIGN PATENT DOCUMENTS

| | | |
|---|---|---|
| WO | 99/61058 | 12/1999 |
| WO | 03/070323 | 8/2003 |

OTHER PUBLICATIONS

Abraham et al., for the Miracle study group, "Cardiac Resynchronization in Chronic Heart Failure," *N Engl J Med*, 2002;346:1845-53.

ACC/AHA Task Force on Practice Guidelines, "Evaluation and Management of Chronic Heart Failure in the Adult," *JACC* 2002;38:2101-13.

Allessie et al., "Regional Control of Atrial Fibrillation by Rapid Pacing in Conscious Dogs," *Circulation* 1991; 84:1689-97.

Ansalone et al., "Bi-ventricular Pacing I Heart Failure:Back to Basics in the Pathophysiology of Left Bundle Branch Block to Reduce the Number of Nonresponders," *Am J Cardiol* 2003;91:55F-61F.

Auricchio et al., "Cardiac Resynchronization Therapy: Current State of the Art," *Circulation* 2004; 109:300-307.

Bardy et al., "The Totally Subcutaneous ICD System (The S-ICD)," *PACE*. 2002; 24,578.

Becker et al, "Suppression of Atrial Fibrillation by Multisite and Septal Pacing in a Novel Experimental Model", *Cardiovascular Research* 2001;54(2):476-481.

Bradley et al., "Cardiac Resynchronization and Death from Progressive Heart Failure: A Meta-Analysis of Randomized Controlled Trials," *JAMA* 2003;289:730-740.

Camm et al., Chapter 6: Nonpharmaceutical treatment of atrial fibrillation, In *Atrial Fibrillation. Facts from Yesterday—Ideas for tomorrow*. Futura Publishing Company, Inc., Armonk, NY, 1994, pp. 125-147.

Dalecki et al., "Effects of Pulsed Ultrasound on the Frog Heart: I. Thresholds for Changes in Cardiac Rhythm and Aortic Pressure," *Ultrasound in Med. & Biol.* 1993; 19:385-390.

Dalecki et al., "Effects of Pulsed Ultrasound on the Frog Heart: II. An Investigation of Heating as a Potential Mechanism," *Ultrasound in Med. & Biol.* 1993; 19:391-398.

Dalecki et al., "Thresholds for premature ventricular contractions in frog hearts exposed to lithotriper fields," *Ultrasound in Med. & Biol.* 1991; 17:341-346.

Daoud et al., "Implantation Techniques and Chronic Lead Parameters of Biventricular Pacing Dual-chamber Defibrillators," *J Cardiovasc Electrophysiology* 2002; 13:964-970.

Daubert et al., "Permanent Left Ventricular Pacing With Transvenous Leads Inserted Into The Coronary Veins," *PACE* 1998;21;239-245.

Daubert et al., "Use of Specifically Designed Coronary Sinus Leads for Permanent Left Ventricular Pacing: Preliminary Experience," *PACE*, 1997; 20: II-NASPE Abstract Apr. 17, 1997.

David Trial Investigators, "The Dual Chamber and VVI Implantable Defibrillator (David) Trial," *JAMA* 2002;288:3115-3123.

Deshmukh et al. "Direct His-bundle pacing: present and future," *PACE* 2004;27[Pt. II]:862-70.

Ellenbogen et al., "Detection and Management of An Implantable Cardioverter Defibrillator Lead Failure," *JACC*. 2003;41:73-80.

Feldman et al, "Comparison of medical therapy, resynchronization and defibrillation therapies in heart failure trail (Companion)," Presented at ACC 2003 Late Breaking Clinical Trials, 1 page.

Franz, "Mechano-electrical feedback in ventricular myocardium," *Cardiovascular Research*. 1996; 32:15-24.

Gregoratos et al., ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). *Circulation*. 2002; 106:2145-2161.

Hu et al., "Stretch-Activated Ion Channels in the Heart," *J. Mol. Cell Cardiol*. 1997; 29:1511-1523.

Johnson et al., "Adaptive Pacing During Ventricular Fibrillation," *PACE* 2003;26:1824-36.

Kalman J.M. et al, "Regional Entrainment of Atrial Fibrillation in Man", *J Cardiovasc Electrophysiol* 1991;7:867-76.

Kass et al., "Improved Left Ventricular Mechanics from Acute VDD Pacing in Patients with Dilated Cardiomyopathy and Ventricular Conduction Delay," *Circulation* 1999;99:1567-73.

Kenknight B.H. et al, "Regulation Capture of Fibrillating Ventricular Myocardium" Circ Res 1999;77:849-55.retrieve from the Internet:<<http://circres.ahajournals.org/cgi/content/full/77/4/849>>.

Kohl et al., Stretch-Induced Changes in Heart Rate and Rhythm: Clinical Observations, Experiments and Mathematical Models. *Progress in Biophysics & Molecular Biology*, 1999; 71:91-138.

Kohl et al., "Sudden Cardiac Death by Commotio Cordis: Role of Mechano-Electrical Feedback," *Cardiovascular Research*, 2001; 50:280-289.

Leclercq et al, "Is Dual Site Better than Single Site Atrial Pacing in the Prevention of Atrial Fibrillation?" *PACE* 2000;23:2102-7.

Leclercq et al., "Systolic Improvement and Mechanical Resynchronization does not Require Electrical Synchrony in the Dilated Failing Heart with Left Bundle-Branch Block", *Circulation* 2002;106:1760-1763.

Leclerq et. al., "Acute Hemodynamic Effects of Biventricular DDD Pacing in Patients with End-Stage Heart Failure", JACC 1998;32:1825-1831.

Lee et al., "Effect of implantable Defibrillators of Arrhythmic Events and Mortality in the Multicenter Unsustained Tachycardia Trial," *Circulation*. 2002; 106:233-238.

Linde et al., "Long-Term Benefits of Biventricular Pacing in Congestive Heart Failure: From the Multisite Stimulation in Cardiomyopathy (MUSTIC) Study", *J Am Coll Cardiol* 2002;40:111-118.

Miracle Trial Investigators, "Combined Cardiac Resynchronization and Implantable Cardioversion Defibrillation in Advanced Heart Failure: the Miracle ICD Trial," *JAMA* 2003;289:2685-2694.

Mirza et al, "Biatrial Pacing for Paroxysmal Atrial Fibrillation", *J Am Coll Cardiol* 2002;40:457-463.

Moss et al., "Phophylactic Implantation of a Defibrillator in Patients with Myocardial Infarction and Reduce Ejection Fraction," *N Engl J Med*. 2002; 346:877-933.

Niehaus et al., "Non-Contact Cardiac Stimulation with locused Ultrasound Pulses," *PACE* 2003: 26:1023.

Nielsen et al., "A Randomized Comparison of Atrial and Dual-Chambered Pacing in 177 Consecutive Patients With Sick Sinus Syndrome," *J Am Coll Cardiol* 2003;42:614-623.

Nolte et al., "Mechanically Induced Ventricular Extrasystoles in the Isolated Perfused Guinea-Pig Heart," *Arzneim.-Forsch/Drug Research*. 1987; 37(11): 1025-1029.

Peschar et al., "Left Ventricular Septal and Apex Pacing for Optimal Pump Function in Canine Hearts," *J Am Coll Cardiol*, 2003;41:1218-26.

Reiter et al., "Effects of Mechano-Electrical Feedback: Potential Arrhythmogenic Influence in Patients With Congestive Heart Failure," *Cardiovascular Research*, 1996; 32:44-51.

Smailys et al., "Investigation of the Possibilities of cardiac Defibrillation by Ultrasound," *Resuscitation*, 1981; 9:233-242.

Sowton, "Clinical Results with the Tachylog Antitachycardia Pacemaker", *PACE* 1984; 7(Part II):1313-1317.

Tacker, Chapter 1: Fibrillation causes and criteria for defibrillation. In *Defibrillation of the Heart. Tacker*, WA, ed. Mosby-Year Book, Inc., St. Louis, Missouri, 1994, pp. 1-14.

The Antiarrhythmics Versus Implantable Defibrillators (AVID) Investigators, "A Comparison of Antiarrhythmic Drug Therapy with Implantable Defibrillators in Patients Resuscitated from Near Fatal Ventricular Arrhythmias," *N Engl J Med* , 1997;337:1576-1583.

Valls-Bertault et al., "Adverse Events with Transvenous Left Ventricular Pacing in Patients with Sever Heart Failure: Early Experience from a Single Centre," *Europace*, 2001;3:60-63.

Warren et al., "Clinical Evaluation of Automatic Tachycardia Diagnosis by an Implanted Device", *PACE* 1986;9 (Part II):1079-1083.

International Search Report and Written Opinion of PCT Application No. PCT/US05/46532, dated Jun. 23, 2008, 8 pages total.

\* cited by examiner

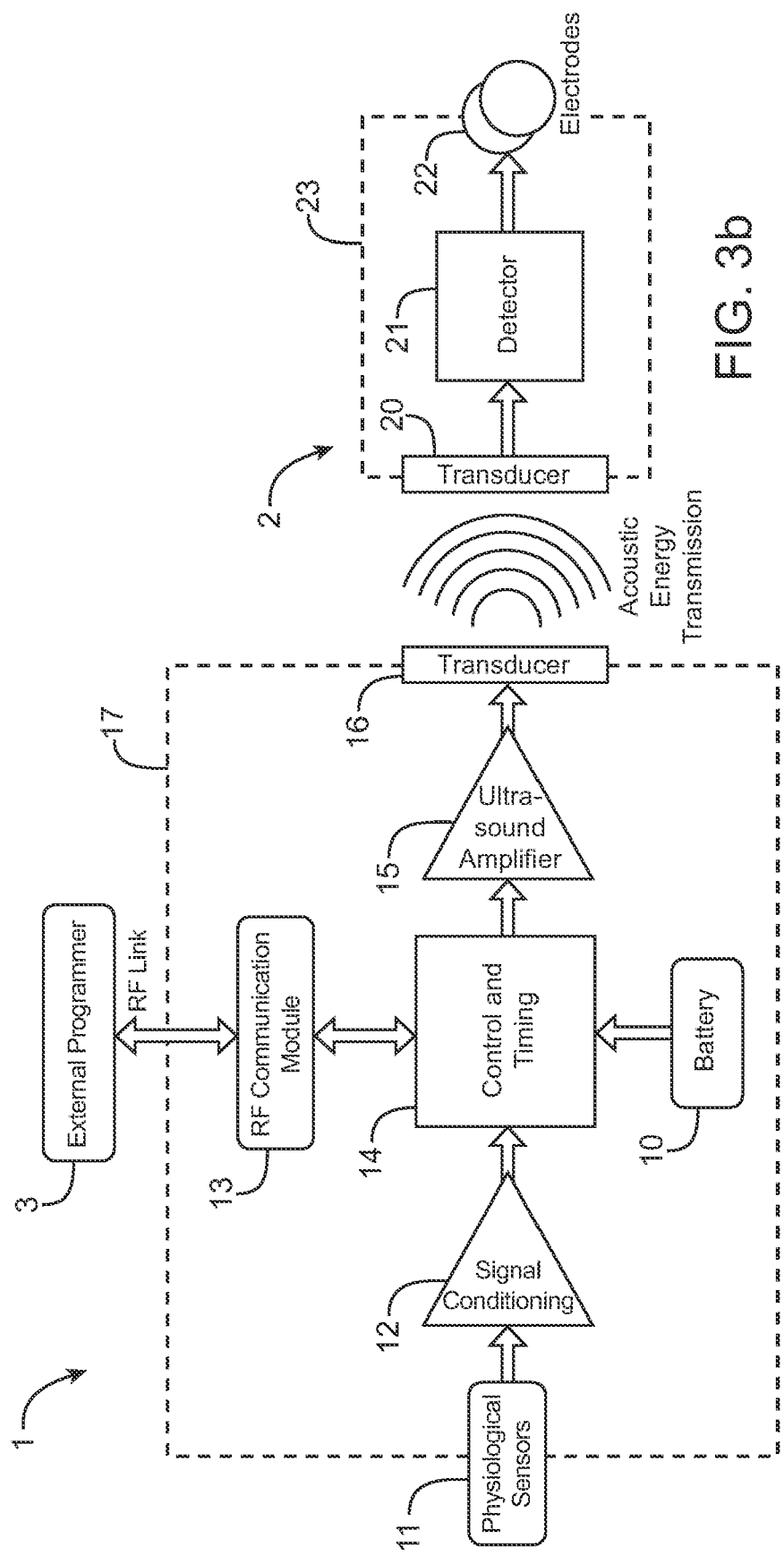

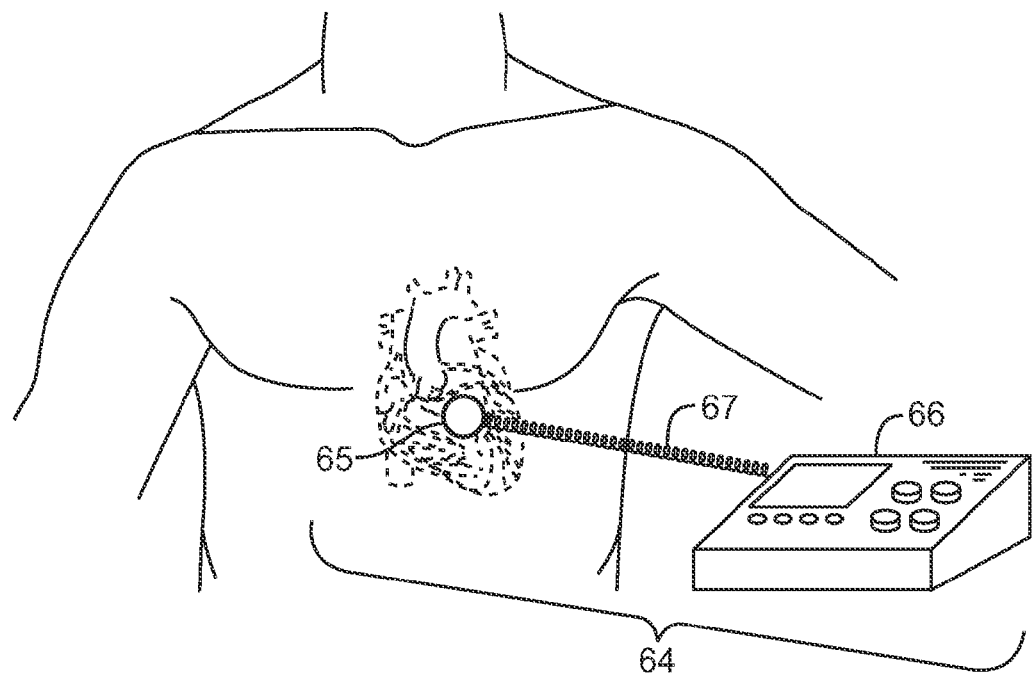
FIG. 10A
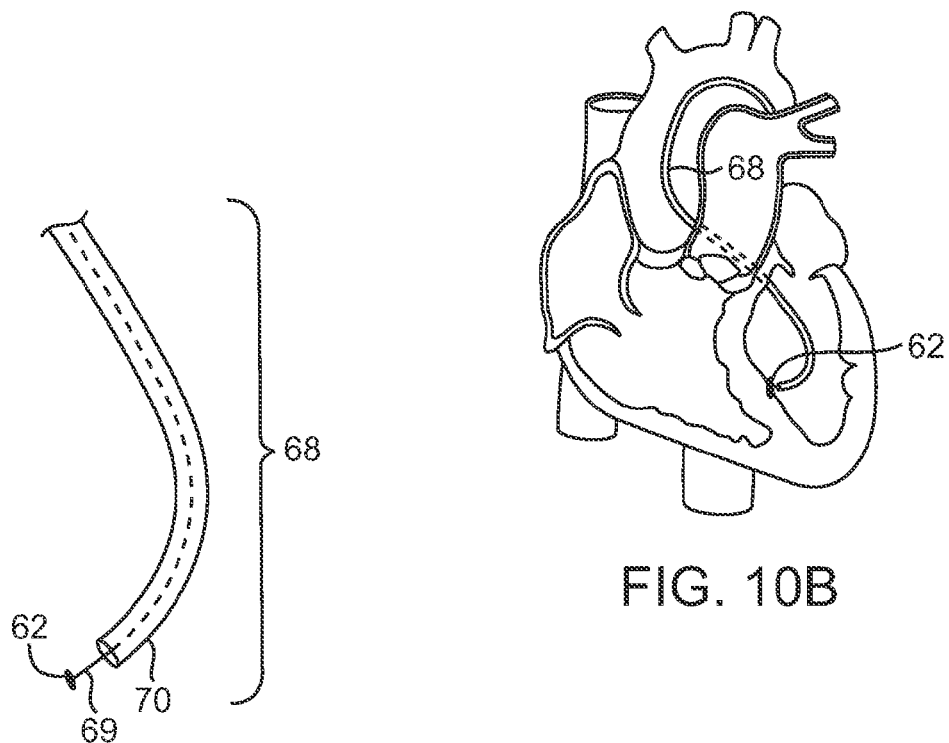
FIG. 10B
FIG. 10C

LEADLESS TISSUE STIMULATION SYSTEMS AND METHODS

CROSS-REFERENCES TO RELATED APPLICATIONS

This application claims the benefit and priority of the following: U.S. Provisional Application No. 60/689,606, filed on Jun. 9, 2005; U.S. Provisional Application No. 60/639,027, filed on Dec. 21, 2004; and U.S. Provisional Patent Application No. 60/639,037, filed on Dec. 21, 2004, the full disclosures of which are incorporated herein by reference.

The subject matter of this application is also related to that of application Ser. No. 11/315,524, filed on Dec. 21, 2005, which claims the benefit of Provisional Application No. 60/639,056, filed on Dec. 21, 2004, the full disclosures of which are incorporated herein by reference.

BACKGROUND OF THE INVENTION

1. Field of the Invention

The systems and methods of this invention relate to electrical stimulation of the heart and other body tissues by means of an implantable device. Specifically the present invention relates to systems and methods for providing such stimulation without the use of conventional lead/electrode systems. More specifically, the present application provides systems and methods for treatment of heart failure and for terminating heart arrhythmias with implantable pacing systems and components.

Electrical stimulation of body tissues is used throughout medicine for treatment of both chronic and acute conditions. Among many examples, peripheral muscle stimulation is reported to accelerate healing of strains and tears, bone stimulation is likewise indicated to increase the rate of bone regrowth/repair in fractures, and nerve stimulation is used to alleviate chronic pain. A commonly implanted device utilizing electrical stimulation is the cardiac pacemaker. Further there is encouraging research in the use of electrical stimulation to treat a variety of nerve and brain conditions, such as essential tremor, Parkinson's disease, migraine headaches, functional deficits due to stroke, and epileptic seizures.

Devices to provide such stimulation may be applied externally in some cases, or in other cases it is more advantageous to implant all or part of the device. This invention pertains to devices in which at least one portion providing direct electrical stimulation to the body tissue is either permanently or temporarily implanted. Such devices include pacemakers, implantable defibrillators, and other devices for stimulating cardiac and other tissues.

Electrical energy sources connected to electrode/lead wire systems have typically been used to stimulate tissue within the body. The use of lead wires is associated with significant problems such as complications due to infection, lead failure, and electrode/lead dislodgement.

The requirement for leads in order to accomplish stimulation also limits the number of accessible locations in the body. The requirement for leads has also limited the ability to stimulate at multiple sites (multisite stimulation). For instance, the treatment of epilepsy could require a minimum of perhaps 5 or 6 stimulation sites. Other diseases, such as Parkinson's disease, would benefit from more stimulation sites than the two utilized in current systems.

Beyond the problems of outright failure and placement difficulties, pacemaker leads inherently cause problems for pacemaker systems by acting as antennae, coupling electromagnetic interference (EMI) into the pacemaker electronics. Particularly problematic is interference with cardiac electrogram sensing and signal processing circuitry. With the exponential rise in the number of cellular telephones, wireless computer networks, and the like, pacemaker lead induced EMI will continue to spur increased complexity in the design of, and require significant testing of pacemaker devices.

The most commonly implanted stimulation device is the cardiac pacemaker. A pacemaker is a battery-powered electronic device implanted under the skin, connected to the heart by an insulated metal lead wire with a tip electrode. Pacemakers were initially developed for and are most commonly used to treat bradycardia, slow heart rates, which may result from a number of conditions. More recently, advancements in pacemaker complexity, and associated sensing and pacing algorithms have allowed progress in using pacemakers for the treatment of other conditions, notably heart failure (HF) and fast heart rhythms (tachyarrhythmia/tachycardia).

In a common application, pacemaker leads are placed through the skin into a subclavian vein or branch to access the venous side of the cardiovascular system. Such systems can be either single chamber with a lead placed in either the right atrium or right ventricle, or dual chamber systems with one lead placed in contact with the right atrial wall and a second lead placed in contact with the right ventricular wall. For the treatment of HF, through what is commonly known as cardiac resynchronization therapy, bi-ventricular pacing is utilized, requiring that an additional lead be placed in contact with the left ventricle. To access the left ventricle, the third lead is typically advanced into the right atrium, into the orifice of the coronary sinus, and then maneuvered through the coronary sinus veins to a position on the epicardial aspect of the posterolateral or lateral wall of the left ventricle.

Though now less common after nearly five decades of improvement in designs and materials, failure of a pacemaker lead is still a significant risk to the patient—not only for the loss of pacing which may represent a life-threatening event, but also due to the fact that once implanted, pacemaker leads are only extracted with a procedure or surgery of significant risk. Additionally, the location of an existing non-functional lead, if not removable, may prevent implantation of a replacement lead. Pacemaker leads may fail due to a number of reasons including breakage of the insulator or conductor and loose or incompatible connectors.

In biventricular pacing for HF, placement of the third lead to contact the left ventricle remains a significant problem. The coronary sinus is a complicated venous pathway with multiple branches which bend and narrow with considerable variation as they extend distally onto the epicardium of the left ventricle. Placement of the third lead requires significant skill on the part of the physician. In order to provide adequate steerability and pushability, the design of the left ventricular lead or a lead introduction system/device is much more complicated than regular pacing leads. Often the positioning and placement of the left ventricular lead can take over an hour to perform, exposing the patient to increased fluoroscopy radiation and increased procedure risks. In some patients (7.5% in the MIRACLE study) an acceptable lead placement is not possible due to anatomic constraints or phrenic nerve pacing. Additionally, lead dislodgement and loss of pacing have been common complications in the use of these coronary sinus leads (10-20% complication rates within the first 6 months of device placement).

The requirement for a lead to accomplish left ventricular stimulation limits the placement to either the coronary sinus vein as described above or an epicardial placement which uses surgical techniques to place the lead on the epicardium and then tunneling of the lead to the location of the pacing device for connection. Left ventricular leads are not placed inside the heart chamber as they are for the right-sided leads for several reasons. They would have to be chronically situated retrograde across the aortic valve or transeptally across the mitral valve which could cause aortic or mitral valvular insufficiency. The patients would be subject to risk of thromboembolic complications from having leads in the arterial circulation. Retrograde insertion of a pacing lead into the left ventricle via the aorta would require a permanent arterial puncture for lead insertion, permanent aortic regurgitation, and permanent anticoagulation to prevent thrombus formation. Alternatively, atrial transeptal puncture from the right atrium to insert a pacing lead into the left atrium or left ventricle also requires permanent anticoagulation, and for left ventricular sites, would cause mitral regurgitation. Moreover, all pacemaker leads are associated with an incidence of infection, and the risk of valvular endocarditis is greater in the left heart.

In patients receiving a bi-ventricular pacing system, site selection for placement of the left ventricular lead has been found to be critically important in order to provide hemodynamic benefit. Up to 40% of patients receiving bi-ventricular pacing for the treatment of HF do not benefit (i.e. hemodynamic measures and HF functional class do not improve or deteriorate). The most important cause for lack of benefit is thought by experts to be due to suboptimal or incorrect left ventricular stimulation site. However, restrictions imposed by the difficulty of positioning and by the anatomy of the coronary sinus and its branches often limit the ability to select a more optimal left ventricular pacing site. The ability to precisely select the left ventricular site for stimulation in combination with right ventricular stimulation, would aid in the treatment of HF.

Moreover, left ventricular stimulation currently is restricted to sites on the epicardial (outer) surface of the heart; the coronary sinus courses on the epicardium, and surgically implanted left ventricular leads are screwed into the epicardium. Recent data indicates that endocardial (inside lining) or subendocardial (inside layer) stimulation sites in the left ventricle provide additional benefit.

Importantly, clinical trial data now suggest that pacing of the left ventricle alone may result in hemodynamic benefit equivalent to that of bi-ventricular pacing. Thus, a leadless pacing system has the potential to accomplish the benefit of bi-ventricular pacing without the need for a right ventricular pacing lead or electrodes.

It would also be beneficial to provide more physiological right ventricular pacing for patients without HF. In normal physiology, the right ventricle is first stimulated in the upper septal area, and then the impulse travels down specially conducting pathways to the right ventricular apex. However, pacing the right ventricle is virtually always accomplished from a lead tip electrode located in the right ventricular apex, such that the subsequent conduction pathway is abnormal and slow. Clinical trials have recently shown that in patients with and without A-V block, pacing from the right ventricular apex can result in increased total mortality and re-hospitalization for heart failure. Thus it would be advantageous to be able to pace the right ventricle at more physiological locations such as the upper septum. The most physiological location to pace the ventricle in patients with sinus nodal or A-V junction conduction disease is to directly pace the His bundle. However, this location is very difficult to access from the superior (vena cava) approach mandated by lead-based systems that attach to a pectorally implanted pulse generator. It would be beneficial to deliver electrodes from the inferior (vena cava) approach via the femoral veins, in which catheter positioning in the A-V junction region is known to be easier. For instance, in a published series of permanent His bundle pacing, the His bundle was first identified using a temporary catheter inserted via the femoral vein, and this catheter was left in place to mark the location to target the site to implant the permanent pacing lead. In patients with lower conduction disease involving the A-V junction or bundle branches, the most physiological pacing sites have been found to be the left ventricular septum or left ventricular apex. These are locations in proximity to the specialized Purkinje conduction network. These locations are not accessible using current transvenous lead-based pacing systems. It would be advantageous to be able to select the pacing site in order to model more normal conduction.

Still another advantage of a leadless pacemaker system would be increased compatibility with magnetic resonance imaging (MRI). Current pacemaker pulse generators are made of materials and/or contain shielding that is generally compatible with the high static and alternating magnetic fields of MRI. However, lead wires are typically constructed with coiled metallic conductors, which are subject to induced currents from the magnetic field. Such currents can cause unwanted stimulation of the heart, and potentially damage the pacemaker pulse generator. A leadless pacemaker system will obviously eliminate the problem of current induced in the lead wires, though proper materials selection and shielding will still have to be employed in the design of the implantable components.

Recently, the concept of a leadless, subcutaneous implantable defibrillator has been proposed e.g. U.S. Pat. No. 6,647,292 (Bardy). In this concept high energy electrical waveforms are delivered between electrodes implanted in subcutaneous chest regions creating sufficient energy density within the thoracic volume to terminate ventricular tachycardia (VT) or ventricular fibrillation (VF). This uses the same electrical field density concept for VT/VF termination as external application or as implanted defibrillator devices with electrodes on leads in the heart. In external defibrillation, energy is delivered between electrodes on the skin surface. In this subcutaneous approach electrodes are implanted beneath the skin but not in contact with the heart. In common implantable systems one of the defibrillation electrodes may consist of the metal enclosure of the implanted controller with the other electrode a coil on a lead placed in the right side (right ventricle) of the heart.

The subcutaneous implantable defibrillator system has no direct contact with cardiac tissue so there are added difficulties incorporating pacing therapy compared to lead-based pacemakers. To pace with subcutaneous electrodes, a sufficient electrical field must be created between two electrodes across the chest volume in order to reach pacing stimulation thresholds in the heart. This method also has no capability to precisely localize the electrical effect in the heart. Since this is a field effect, all muscles and nerves in the chest are exposed to the electrical field. The pacing pulse energy levels required to stimulate cardiac tissue using this electrical field approach are sufficiently high that chest muscle contractions and pain sensations would be associated with subcutaneous pacing. While pain occurs with high energy defibrillating discharges of all implantable defibrillators, no pain occurs with low-energy pacing using intracardiac leads. A subcutaneously implanted device implementing pacing would cause patient pain and would not be accepted when compared to a pain-free alternative. It would be highly advantageous to have a leadless system that would be capable of high energy defibrillation and also contain painless pacing capability.

In addition to using high energy electrical waveforms for the termination of VT/VF, lead-based implantable defibrillator systems typically also contain pacing algorithms that are effective in terminating VT/VF, referred to as antitachycardia pacing (ATP). For ATP, both the lead-based implantable system and the leadless subcutaneous system concepts have limitations in selecting the location of the pacing application, particularly in the left side of the heart. VT can be readily terminated using low voltage pacing stimulation if the site of the pacing is near the ventricular tachycardia focus or reentrant circuit. However, this is usually in the left ventricle, and close to the endocardium. As noted above, current pacemaker/defibrillator devices incorporate antitachycardia pacing but the pacing site is limited to the right ventricular lead or is subject to the same limitations previously described for left-sided lead placements. Further, right-sided locations have been shown to be less effective in electrophysiology laboratory testing, especially for VT's of high rate which are more serious. Pacing stimuli must stimulate cardiac tissue in the excitable region (excitable gap) of the VT reentry circuit in order to terminate the VT. Most VT circuits are located in the subendocardial layer of the left ventricle. For more rapid rate VT's, the excitable gap is small and the pacing stimuli must be very close to the VT reentry circuit for successful VT termination. In current pacemaker/defibrillator devices, if antitachycardia pacing is ineffective in terminating VT, painful high energy electrical field shocks are delivered. Therefore, it would be advantageous to be able to select the pacing site, particularly near the endocardium and in the left ventricle. Having the capability to select the location for a left ventricular lead for terminating episodes of ventricular tachycardia using antitachycardia pacing techniques would be expected to be more effective compared to current devices.

Another limitation of both the requirement of having leads and of having limited access to the left heart is in the emerging area of multisite pacing for termination of atrial and ventricular fibrillation. These arrhythmias typically arise in and are maintained by the left atrium and left ventricle. Studies have demonstrated the presence of excitable gaps within the tissue during atrial fibrillation (animal and human studies) and ventricular fibrillation (animal studies). By placing and stimulating at multiple pacing sites, regional pacing capture can be obtained during these arrhythmias. This means that if stimulation is delivered at the appropriate timing to a sufficient number of sites, in the appropriate locations, termination of atrial and ventricular fibrillation is possible. The advantage of terminating fibrillation with selected site left ventricular pacing would be the avoidance of painful high energy shocks. In this application the capability for left-sided stimulation and multi-sites of stimulation would be advantageous.

In addition to the termination of tachyarrhythmias, implanted pacemakers and defibrillators have been used to prevent tachyarrhythmias. In patients receiving permanent pacemakers, the dual chamber (DDD) mode has been shown to result in fewer episodes of AF compared to single chamber (VVI) mode in several large clinical trials. DDD pacing that incorporates simultaneous multisite stimulation of both the high right atrium and CS ostium has also been compared to standard single atrial site DDD pacing for the suppression of AF, showing a modest reduction of AF episodes. Atrial stimulation at a site or multiple sites other than the usual right atrial appendage may be advantageous for the prevention of atrial fibrillation by shortening total atrial activation time. Right atrial sites in Koch's triangle and Bachman's bundle may reduce atrial activation time by stimulating near or within atrial conduction tracts or within other tracts that are part of the normal conduction pathway. In an experimental canine model (Becker), either 4 pacing sites (2 in RA and 2 in LA) or one in the interatrial septum were required for suppression of AF. While these results are very promising, they present a technical obstacle for current pacemaker systems. The use of multisite pacing incorporating pacing sites in the left atrium for the suppression of AF has not been evaluated in humans because of all the issues of using multiple leads and in using leads within the left heart.

It follows that if AF may be able to be suppressed with multisite atrial pacing (especially in the left atrium), that VF may be able to be suppressed with multisite ventricular pacing (especially in the left ventricle). However, the difficulties associated with the implantation of multiple leads in the left ventricle has rendered this form of prevention impossible.

For these reasons, it would be desirable to accomplish stimulation without the need for lead wires. In this application we describe methods and apparatus, using acoustic energy for an implantable leadless stimulator system, that overcome limitations in pacing site selection. In co-pending applications we further describe improved stimulating devices. Methods and systems to evaluate and optimize positioning for implantation of this invention are described herein.

2. Description of the Background Art

U.S. Pat. No. 3,659,615, Enger; Encapsulated Non-Permeable Piezoelectric Powered Pacesetter, May/1972

U.S. Pat. No. 4,256,115, Bilitch; Leadless Cardiac Pacer, March/1981

U.S. Pat. No. 4,690,144, Rise et al; Wireless Transcutaneous Electrical Tissue Stimulator, September/1987

U.S. Pat. No. 5,170,784, Ramon et al; Leadless Magnetic Cardiac Pacemaker, December/1992

German Patent DE4330680 (abandoned), Zwicker; Device for Electrical Stimulation of Cells within a Living Human or Animal, March/1995

U.S. Pat. No. 5,405,367, Schulman et al; Structure and Method of Manufacture of an Implantable Microstimulator, April/1995

U.S. Pat. No. 5,411,535, Fujii et al; Cardiac Pacemaker Using Wireless Transmission, March/1995

U.S. Pat. No. 5,749,909, Schroeppel et al; Transcutaneous Energy Coupling Using Piezoelectric Device, May/1998

U.S. Pat. No. 5,751,539, Stevenson et al; EMI Filter for Human Implantable Heart Defibrillators and Pacemakers, May/1998

U.S. Pat. No. 5,766,227, Nappholz et al; EMI Detection in an Implantable Pacemaker and the like, May/1998

U.S. Pat. No. 5,814,089, Stokes et al; Leadless Multisite Implantable Stimulus and Diagnostic System, September/1998

U.S. Pat. No. 5,817,130, Cox et al; Implantable Cardiac Cardioverter/Defibrillator with EMI Suppression Filter with Independent Ground Connection, October/1998

U.S. Pat. No. 5,978,204, Stevenson; Capacitor with Dual Element Electrode Plates, November/1999

U.S. Pat. No. 6,037,704, Welle; Ultrasonic Power Communication System, March/2000

U.S. Pat. No. 6,366,816, Marchesi; Electronic Stimulation Equipment with Wireless Satellite Units, April/2002

U.S. Patent Application Publication 2002/0077673, Penner et al; Systems and Methods for Communicating with Implantable Devices, June/2002

U.S. Pat. No. 6,424,234, Stevenson; Electromagnetic Interference (EMI) Filter and Process for Providing Electromagnetic Compatibility of an Electronic Device while in the Presence of an Electromagnetic Emitter Operating at the Same Frequency, July/2002

U.S. Pat. No. 6,445,953, Bulkes et al; Wireless Cardiac Pacing System with Vascular Electrode-Stents, September/2002

U.S. Pat. No. 6,654,638, Sweeney; Ultrasonically Activated Electrodes, November/2003

U.S. Patent Application Publication 2004/0172083, Penner; Acoustically Powered Implantable Stimulating Device, September/2004

U.S. Pat. No. 4,280,502 to Baker, Jr. et al., Tachycardia arrester, July/1981

U.S. Pat. No. 4,561,442 to Vollmann et al., Implantable cardiac pacer with discontinuous microprocessor programmable antitachycardia mechanisms and patient data telemetry, December/1985

U.S. Pat. No. 4,181,133 to Kolenik et al., Programmable tachycardia pacer, January/1980

U.S. Pat. No. 3,832,994 to Bicher et al., Cardiac Monitor, Septbmer/1974

U.S. Pat. No. 3,693,627 to Berkovits, Stimulator for Treatment of Tachycardia with a Burst of Stimuli Having a Continuously Variable Rate, September/1972

U.S. Pat. No. 3,698,398 to Berkovits, Rate-scanning Pacer for Treatment of Tachycardia, October/1972

U.S. Pat. No. 4,577,633 to Berkovits et al., Rate scanning demand pacemaker and method for treatment of tachycardia, 3/1086

U.S. Pat. No. 5,063,928 to Grevis et al., Apparatus and method for detecting and treating cardiac tachyarrhythmias, November/1991

U.S. Pat. No. 3,939,844 to Peuignot et al., Method and apparatus for stimulating a heart to eliminate rhythmic abnormalities, especially tachycardias, February/1976

U.S. Pat. No. 3,942,534 to Allen et al., Device for terminating tachycardia, March/1976

U.S. Pat. No. 4,830,006 Haluska et al., Implantable cardiac stimulator for detection and treatment of ventricular arrhythmias, May/1989

U.S. Pat. No. 5,674,251 Combs et al., Method and apparatus for treatment of atrial fibrillation, October/1997

U.S. Pat. No. 6,078,837 Peterson et al., Method and apparatus for treatment of fibrillation, June/2000

U.S. Pat. No. 6,754,531 Kroll et al., Anti-tachycardia pacing methods and devices, June/2004

U.S. Pat. No. 6,856,835 to Bardy, et al., Biphasic waveform for anti-tachycardia pacing for a subcutaneous implantable cardioverter-defibrillator, February/2005

U.S. Pat. No. 6,834,204 to Osteroff et al., Method and apparatus for inducing defibrillation in a patient using a T-shock waveform, December/2004

U.S. Pat. No. 6,788,974 to Bardy et al., Radian curve shaped implantable cardioverter-defibrillator canister, September/2004

U.S. Pat. No. 6,754,528 to Bardy et al. Apparatus and method of arrhythmia detection in a subcutaneous implantable cardioverter/defibrillator, June/2004

U.S. Pat. No. 6,721,597 to Bardy et al. Subcutaneous only implantable cardioverter defibrillator and optional pacer, April/2004

U.S. Pat. No. 6,671,547 to Lyster et al. Adaptive analysis method for an electrotherapy device and apparatus, December/2003

U.S. Pat. No. 6,647,292 to Bardy et al. Unitary subcutaneous only implantable cardioverter-defibrillator and optional pacer, November/2003

Allessie M, Kirchof C, Scheffer G J, Chorro F, Brugado J k "Regional Control of Atrial Fibrillation by Rapid Pacing in Conscious Dogs," *Circulation* 1991;84:1689-97.

DAVID Trial Investigators, "The Dual Chamber and VVI Implantable Defibrillator (DAVID) Trial," *JAMA* 2002; 288:3115-3123.

Johnson P L, Newton J C, Rollins D L, Smith S M, Ideker R E, "Adaptive Pacing during Ventricular Fibrillation, *PACE* 2003;26:1824-36.

Kass D A, Chen C-H, Curry C, Talbot M, Berger R, Fetics B, Nevo E, "Improved Left Ventricular Mechanics from Acute VDD Pacing in Patients with Dilated Cardiomyopathy and Ventricular Conduction Delay," *Circulation* 1999;99:1567-73.

Abraham W T, Fisher W G, Smith A L, Delurgio D B, Leon A R, Loh E, Kocovic D Z, Packer, M, Clavell A L, Hayes D L, Ellestad M, Messenger J, for the MIRACLE study group, "Cardiac Resynchronization in Chronic Heart Failure," N Engl J Med, 2002;346:1845-53.

Becker R. et al, "Suppression of Atrial Fibrillation by Multisite and Septal Pacing in a Novel Experimental Model", Cardiovascular Research 2001;54:476-481.

Kalman J. M. et al, "Regional Entrainment of Atrial Fibrillation in Man", J Cardiovasc Electrophysiol 1991;7:867-76.

KenKnight B. H. et al, "Regional Capture of Fibrillating Ventricular Myocardium" Circ Res 1999;77:849-55.

Leclercq J. F. et al, "Is Dual Site Better than Single Site Atrial Pacing in the Prevention of Atrial Fibrillation?" PACE 2000;23"2102-7.

Mirza I. et al, "Biatrial Pacing for Paroxysmal Atrial Fibrillation", J Am Coll Cardiol 2002;40:457-463.

Sowton, E., "Clinical Results with the Tachylog Antitachycardia Pacemaker", PACE 1984;7(Part II):1313-1317.

Warren, J. et al., "Clinical Evaluation of Automatic Tachycardia Diagnosis by an Implanted Device", PACE 1986;9 (Part II):1079-1083.

Ansalone G, Giannantoni P, Ricci R, Trambaiolo P, Fedele F, Santini M, "Bi-ventricular pacing I heart failure:back to basics in the pathophysiology of left bundle branch block to reduce the number of nonresponders," *Am J Cardiol* 2003;91:55F-61F.

Auricchio A and Abraham W T, "Cardiac resynchronization therapy: current state of the art," *Circulation* 2004;109: 300-307.

Deshmukh P M and Romanyshyn M, "Direct His-bundle pacing: present and future," *PACE* 2004;27 [Pt.II]:862-70.

Peschar M, de Swart H, Michels K J, Reneman R S, and Prinzen F W, "Left ventricular septal and apex pacing for optimal pump function in canine hearts," *J Am Coll Cardiol* 2003;41:1218-26.

BRIEF SUMMARY OF THE INVENTION

The present invention provides methods and devices to electrically stimulate cardiac muscle and other body tissue utilizing acoustic energy to transmit both energy and signal information from a first implanted device to a second implanted device. The first implanted device, generally referred to as the controller-transmitter or acoustic controller-transmitter, provides appropriate timing and control functions and transmits acoustic energy to the second device. The second implanted device, generally referred to as the receiver-stimulator, receives the acoustic energy and converts it into electrical energy and applies that electrical energy to stimulating electrodes. The second device is adapted to be permanently implanted at a location where it is desired to provide electrical stimulus, with stimulating electrodes in direct contact with the cardiac muscle or other body tissue. Optionally, two or more receiver-stimulators may be implanted to be controlled by a single controller-transmitter.

A cardiac pacemaker (or defibrillator/cardioversion unit as described below) employing ultrasonic energy transfer according to the present invention comprises an implantable receiver-stimulator device adapted to be implanted in or attached to any desired location either endocardially, epicardially, or intramyocardially. Various minimally invasive, transvascular techniques and tools (e.g. catheters, stylets) would be adapted and used to deliver, place, embed, and secure the receiver-stimulator device to these locations. The receiver-stimulator would additionally be adapted to provide permanent attachment to the implant site including possibly the use of helical coils, barbs, tines, clips, or the like. Chronic endothelialization would be encouraged by design features such as tines or irregularities in surface, or by bonding onto its outer surface materials which are known to stimulate cellular growth and adhesion. Alternatively, the receiver-stimulator could be adapted for implantation in the coronary vasculature at preferred sites for stimulation, e.g., being incorporated into a stent-like platform suitable for intravascular delivery and deployment. In a specific embodiment, the device could reside on the outer surface of a stent and be held in place between the outer stent wall and the inner vessel wall. Functionally, the receiver-stimulator device comprises 1) an ultrasound transducer to receive the acoustic energy from a controller-transmitter device and transform it into electrical energy, 2) an electrical circuit to transform the alternating electrical energy into a direct current or waveform having other characteristics, and 3) electrodes to transfer the electrical energy to the myocardium. The receiver-stimulator would use signal information from the acoustic energy transmission to configure the electrical output, for example the pulse width of the transmission would determine the pulse duration/width of the electrical output waveform. Additionally, the receiver-stimulator may comprise circuitry for additional control logic, for example selecting activation of individual receiver-stimulators (on-off control), timing delays, waveform shape adjustments, or the like. In particular, when more than one receiver-stimulator is implanted to be controlled by a single controller-transmitter, the transmitted energy signal may contain addressing or selection information identifying which receiver-stimulator is to be activated at any particular time.

Subsequently, a controller-transmitter device would be implanted subcutaneously utilizing known surgical techniques (above or beneath the pectoral muscles) near the heart; this device containing some or most or all elements of currently available pacemaker systems, with specific adaptations pertinent to this invention. Such typical pacemaker elements may include a power source, pacemaker control and timing circuitry, a sensing system possibly comprised of ECG sensing electrodes, motion detectors, body or other temperature sensors, pressure sensors, impedance sensors (e.g., for measuring respiration cycles or lung edema), or other types of physiologic sensors, signal conditioning and analysis functions for the various electrodes and detectors, and a system to communicate with an outside console for data transmission, diagnostic, and programming functions typically through a radiofrequency (RF) link. Additionally, the controller-transmitter device would contain an ultrasound amplifier and an ultrasound transducer to generate acoustic energy, and transmit such energy in the general direction of the heart and specifically in the direction of the implanted receiver-stimulator device. The duration, timing, and power of the acoustic energy transmission would be controlled as required, in response to detected natural or induced physiological events or conditions, and per known electrophysiological parameters, by the pacemaker control electronics.

A single receiver-stimulator device may be implanted as described above for single site pacing; additionally it would be possible to implant a plurality of receiver-stimulator devices which would stimulate either simultaneously by receiving the same transmitted acoustic energy, or sequentially through fixed or programmable delays after receiving the same transmitted acoustic energy, or independently by responding only to signal information of the transmitted acoustic energy of a specific character (i.e., of a certain frequency, amplitude, or by other modulation or encoding of the acoustic waveform) intended to energize only that specific device.

In a first preferred embodiment a leadless cardiac pacemaker would be employed as a left ventricular pacemaker functioning as a "slave" pacemaker to an implanted conventional (i.e., utilizing leads/electrodes) right heart pacemaker, either a single or preferably a dual chamber type. The purpose of such a slave system would be to provide left ventricular pacing synchronous with the right ventricular pacing provided by the right heart pacemaker as an advantageous treatment for patients with HF, but without necessitating the placement of a left ventricular lead.

In such an embodiment the receiver-stimulator would be implanted at a desired location within the left ventricle, preferably fully embedded within the myocardium. A specialized controller-transmitter would then be implanted subcutaneously at a location allowing insonification of the implanted receiver-stimulator. The specialized "slave" controller-transmitter would include sensing electrodes on or incorporated into its external surface and signal processing circuitry and algorithms to allow it to detect pacing artifact signals from an implanted conventional right heart pacemaker and/or the patient's electrogram (electrocardiographic recording). Signal processing and specialized algorithms would differentiate pacing artifact signals, native cardiac electrogram signals occurring from intrinsic atrial and/or ventricular activation, and/or native cardiac electrogram signals occurring from non-intrinsic atrial and/or ventricular activation initiated from pacing. The slave controller-transmitter would then respond to the right atrial or right ventricular or both pacing artifact signals from the right heart pacemaker, or would respond to detected intrinsic or non-intrinsic activation, and transmit acoustic energy to the implanted receiver-stimulator in order to produce a left ventricular stimulation at the desired time in relation to the right atrial and/or right ventricular paced artifact or detected/sensed cardiac event. For example, when transmission occurs immediately upon the detection of a right ventricular pacing artifact, a left ventricular pacing stimulus is delivered by the receiver-stimulator pacing output in the left ventricle to produce bi-ventricular pacing therapy.

Alternately, the implanted controller-transmitter could be adapted to work in conjunction with a conventional bi-ventricular pacemaker typically having three leads for the right atrium, right ventricle, and left ventricle. In one adaptation, in order to eliminate the requirement to place the left ventricular lead, the controller-transmitter would connect via a special wire to the conventional pacemaker's left ventricular output. The controller-transmitter would then detect the conventional pacemaker's left ventricular pacing output from the special wire and immediately transmit acoustic energy to activate the receiver-stimulator implanted into the left ventricle. Such a system would offer elimination of the left ventricular lead and require only a simple controller-transmitter unburdened by sensing electrodes and associated signal processing circuitry and algorithms. In another adaptation, the input for the left ventricular lead in the conventional bi-ventricular pacemaker header could be sealed off, and the specialized "slave" controller-transmitter would operate as described in the paragraph above.

Another preferred embodiment is a leadless stand alone single chamber pacemaker. Such an embodiment would utilize the same or a similar implantable receiver-stimulator device as described above, however in this case it would be implanted into or attached to the right atrium of the heart in order to provide right atrial pacing, or implanted into or attached to either the right ventricle or left ventricle of the heart in order to provide right or left ventricular pacing. The controller-transmitter would then incorporate most or all of the features of a contemporary single chamber pacemaker device, typically known as an AAI (atrial) or VVI (ventricular) mode pacing. Such conventional pacemakers commonly utilize right atrial or right ventricular leads for treatment of bradyarrhythmias, or slow heart rate. A pacemaker system per this invention would advantageously not require the use of electrical leads of any kind. Moreover, the ability to use a left ventricular lead alone enables the potential hemodynamic benefit of left ventricular pacing compared to a right ventricular pacing without the use of electrical leads of any kind. Further enhancement to this single chamber pacemaker system would include other patient physiological sensor(s) that adjust the patient's paced rate in response to the sensor, e.g., motion detectors. This would provide the capability for AAIR and VVIR modes of pacing.

As described previously, sensing of electrical activity in the body and other patient physiological information such as movement, blood pressure, intracavity impedance changes, or heart sounds would be provided from electrodes and/or other sensors incorporated onto or into or within the housing of the implanted controller-transmitter. In a particular adaptation the transmitting transducer for the controller-transmitter may be used as a sensor for mechanical/motion sensing or for heart sound sensing. Examples for electrical activity sensing include intrinsic cardiac beats, pacemaker pacing artifacts, non-intrinsic cardiac beats initiated by pacemaker pacing outputs, and the like.

In another preferred embodiment of the leadless cardiac pacemaker system a dual chamber pacemaker could be constructed, with function similar to present dual chamber (DDD) pacemakers. Such a pacemaker would be realized by utilizing two implantable receiver-stimulator devices and either one or two implantable controller-transmitter devices. One receiver-stimulator device would be implanted into or attached to the right atrium as described above, the second would be implanted into or attached to the right or left ventricle. One implanted controller-transmitter device would transmit ultrasound to the two implanted receiver-stimulators, causing the receiver-stimulators to provide pacing stimulation to the atrium and ventricle either simultaneously or sequentially. If sequential, timed stimulation to the atrium and ventricle is required, various means to accomplish this could be incorporated into the leadless pacemaker system. In one possibility, a single acoustic waveform would be transmitted at the time necessary to activate the first, typically atrial, receiver-stimulator. The second, typically ventricular, receiver stimulator device would be of a modified design incorporating circuitry and devices to capture and temporarily store the acoustic energy transmitted at the time of atrial stimulation, and after a fixed delay provide this energy to its stimulation electrodes to pace the ventricle. Sequential stimulation could also be accomplished under direct control of the controller-transmitter, possibly utilizing the sequential transmission of acoustic energy at different frequencies, with each receiver-stimulator tuned to respond only to a single unique frequency. Other methods including amplitude modulation, frequency modulation, time-division modulation, or other modulation or encoding of the acoustic waveform would also permit selective and sequential pacing from multiple implanted receiver-stimulator devices. Alternately, two controller-transmitters could be implanted, each configured to transmit acoustic energy only to one specific receiver-stimulator, such configuration achieved either through spatial separation, frequency separation, or other modulation or encoding means as previously described.

In such a dual chamber system, sensing of the electrogram or other patient physiological information would be provided from electrodes and/or other sensors incorporated onto or into or within the housing of the implanted controller-transmitter. Further enhancement to this dual chamber pacemaker system would include other patient physiological sensor(s) that adjust the patient's paced rate in response to the sensor, e.g., motion detectors. This would provide the capability for DDDR modes of pacing.

It can be seen that a dual chamber pacemaker system as described above could be further adapted as a bi-ventricular pacemaker for HF applications. In one embodiment of a bi-ventricular pacemaker the system described above, with appropriate adaptations to the timing considerations between the two pacing signals, could be employed with one receiver-stimulator implanted into the right ventricle and the second receiver-stimulator implanted into the left ventricle. In a further enhancement a third receiver-stimulator could be implanted into the right atrium to provide both dual chamber right-sided pacing with synchronous left ventricular pacing. As described above, means to provide proper sequencing of the multiple pacing stimuli would be employed.

In another preferred embodiment, the leadless cardiac pacemaker system could be used in conjunction with a conventional single chamber or dual chamber implantable cardioverter-defibrillator (ICD) device. The ICD device utilizes a conventional lead/electrode system for (optionally) right atrial and right ventricular sensing and pacing, with defibrillation electrodes combined onto the right ventricular lead. A leadless receiver-stimulator device per this invention could be implanted into the left ventricle, with the combined device incorporating left ventricular pacing, similar to current lead-based CRT-D (integrated ICD and cardiac resynchronization pacing) devices. A receiver-stimulator implanted into the left ventricle would receive acoustic energy from a specialized controller-transmitter to provide stimulus to the left ventricle. The specialized controller-transmitter would be implanted subcutaneously at a location allowing insonification of the implanted receiver-stimulator. Such a system would be advantageous with respect to conventional CRT-D pacemaker/defibrillators, again by eliminating the requirement for the left ventricular lead and the problems associated with its placement.

In another preferred embodiment, the leadless cardiac pacemaker system could be combined with a conventional pacemaker system in a single device. Preferably, such a dual chamber (DDD) pacemaker would utilize a conventional lead/electrode system for right atrial and ventricular sensing and pacing connected to the header of the pulse generator case. The DDD pulse generator case would also contain an acoustic transmitter. In addition to the right atrial and right ventricular pacing accomplished through the conventional leads, a leadless receiver-stimulator device per this invention could be implanted into the left ventricle. The implanted receiver-stimulator would receive acoustic energy from the transmitter incorporated into the otherwise conventional pacemaker to provide stimulus to the left ventricle. Such a system would be advantageous with respect to conventional bi-ventricular pacemakers by eliminating the requirement for the left ventricular lead and the problems associated with the placement thereof.

In still another preferred embodiment, the leadless cardiac pacemaker system could be combined with conventional implantable cardioverter-defibrillator (ICD) technology in a single device. Preferably, such a device would utilize a conventional lead/electrode system for right atrial and ventricular sensing and pacing and defibrillation connected to the header of the pulse generator case. The ICD pulse generator case would also contain an acoustic transmitter. In addition to the right atrial and ventricular pacing and defibrillation accomplished through the conventional leads, a leadless receiver-stimulator device per this invention could be implanted into the left ventricle, with the combined device incorporating bi-ventricular pacing, similar to current lead-based (CRT-D) devices. A receiver-stimulator implanted into the left ventricle would receive acoustic energy from the transmitter incorporated into the otherwise conventional ICD device to provide stimulus to the left ventricle. Such a system would be advantageous with respect to conventional CRT-D pacemaker/defibrillators, again by eliminating the requirement for the left ventricular lead and the problems associated with its placement.

Patients requiring ICD devices have potentially lethal heart rhythms including ventricular tachycardia and fibrillation. Having the additional capability to select the location for a left ventricular lead placement for terminating episodes of ventricular tachycardia using antitachycardia pacing techniques should be more effective compared to current devices. The advantage of terminating tachycardia with selected-site left ventricular pacing may be the avoidance of painful high energy shocks. Moreover, the capability of implanting multiple receiver-stimulators in any heart chamber may allow multisite pacing for the prevention or termination of atrial fibrillation and ventricular fibrillation.

The methods and systems of the present invention may be utilized for antitachycardia pacing (ATP), including prevention algorithms, utilizing acoustic energy to transmit energy and signal information from an acoustic controller-transmitter, which may optionally be implanted or externally located, to one or more implanted receiver-stimulators having electrodes adapted to be implanted in direct contact with cardiac tissue. The acoustic controller-transmitter will usually have ECG or other monitoring means that allow detection of tachycardia, permitting tiered treatment via pacing and optionally higher energy defibrillation and/or cardioversion. In all cases, the energy will be delivered and/or controlled by acoustic signals from the controller-transmitter to the acoustic receiver-stimulator(s). The acoustic receiver-stimulators will convert the acoustic energy into stimulating/pacing/defibrillation/cardioversion electrical energy.

Such a leadless pacing system may advantageously be employed as a stand alone antitachycardia pacemaker. In this embodiment of the present invention, one or more of the receiver-stimulators would be implanted at one or more cardiac sites, and the controller-transmitter may be either a subcutaneously implanted device or an externally applied device.

The leadless pacing system could also be employed along with an implanted conventional (i.e., utilizing leads/electrodes) right heart pacemaker, or along with an implanted conventional right heart pacemaker/cardioverter/defibrillator, either a single or preferably a dual chamber type. The purpose of such a combination of systems would be to provide site-specific pacing for termination or prevention of tachyarrhythmias. Alternatively, the leadless pacing system implanted in combination with a pacemaker/cardioverter/defibrillator provides the patient with a high energy shock capability in case the pacing therapy is ineffective in termination of the arrhythmia.

In a further embodiment a leadless cardiac pacemaker system would be employed along with an implanted subcutaneous, leadless cardioverter/defibrillator. The purpose of such a combination of systems would be to provide a leadless pacing capability for antitachycardia pacing therapy, for backup pacing post shock delivery, and/or for bradycardia pacing support. The implanted subcutaneous, leadless cardioverter/defibrillator provides the patient with a high energy shock capability in case the pacing therapy is ineffective in termination of the arrhythmia or accelerates the tachycardia to fibrillation.

In still further embodiments, a leadless cardiac pacemaker/defibrillator system would be employed as a single integrated high energy electrical shock defibrillator and a leadless site-specific pacing system. The purpose of this integration would be to provide a single subcutaneously implanted controller device.

Similarly, the controller-transmitter can be adapted to be used concomitantly with a leadless, subcutaneous defibrillator to provide the pacing capability. This can be done either as a standalone antitachycardia pacing system, as a defibrillator-pacing system where communication exchanges by a direct connection between the defibrillator and the controller-transmitter, or as a single integrated device system with the capability for acoustic transmission to a receiver-stimulator for pacing (bradycardia backup or for antitachycardia pacing therapy) and for electrical shock for defibrillation.

In further aspects of the present invention, the controller-transmitter device may be implanted at a remote tissue location within or external to the body. The receiver-stimulator device may be either permanently implanted or temporarily placed at a target location with stimulating electrodes in direct contact with the body tissue to be stimulated. By observing changes in a patient response and/or device measurement in response to different combinations of remote and target tissue locations, the sites chosen for permanent implantation may be optimized and selected. Patient response(s) may be any quantitative or qualitative physiologic responses to the stimulation, typically being associated with the desired beneficial response. Device measurement(s) could be signal strength, transmission efficiency, or the like.

Uses for such optimized placement methods include, but are not limited to, applying electrical stimulation for the treatment of peripheral muscle strains and tears, bone fractures, musculoskeletal inflammation, chronic pain, Parkinson's disease, epileptic seizures, high blood pressure, cardiac arrhythmias, heart failure, coma, stroke, hearing loss, dementia, depression, migraine headaches, sleep disorders, gastric motility disorders, urinary disorders, obesity, and diabetes.

The present application describes methods and systems to evaluate effectiveness and optimize the positioning of these implantable leadless systems. Both the controller-transmitter and the receiver-stimulator placements are optimized with these methods. Three methods are described using testing sequences prior to permanent implantation that involve placement of the devices in various locations of the body. In each method, for a set of device locations, a patient response or a device measurement is made. The optimum location is determined based upon the patient responses and/or the device measurements.

BRIEF DESCRIPTION OF THE DRAWINGS

FIGS. 3a and 3b are block diagrams showing the components of the acoustic controller-transmitter and acoustic receiver-stimulators of the present invention.

FIGS. 10a, 10b, and 10c illustrate a system useful for optimizing implantation of the system of FIGS. 9a and 9b in accordance with the principles of the present invention.

DETAILED DESCRIPTION OF THE INVENTION

Figure 1A:
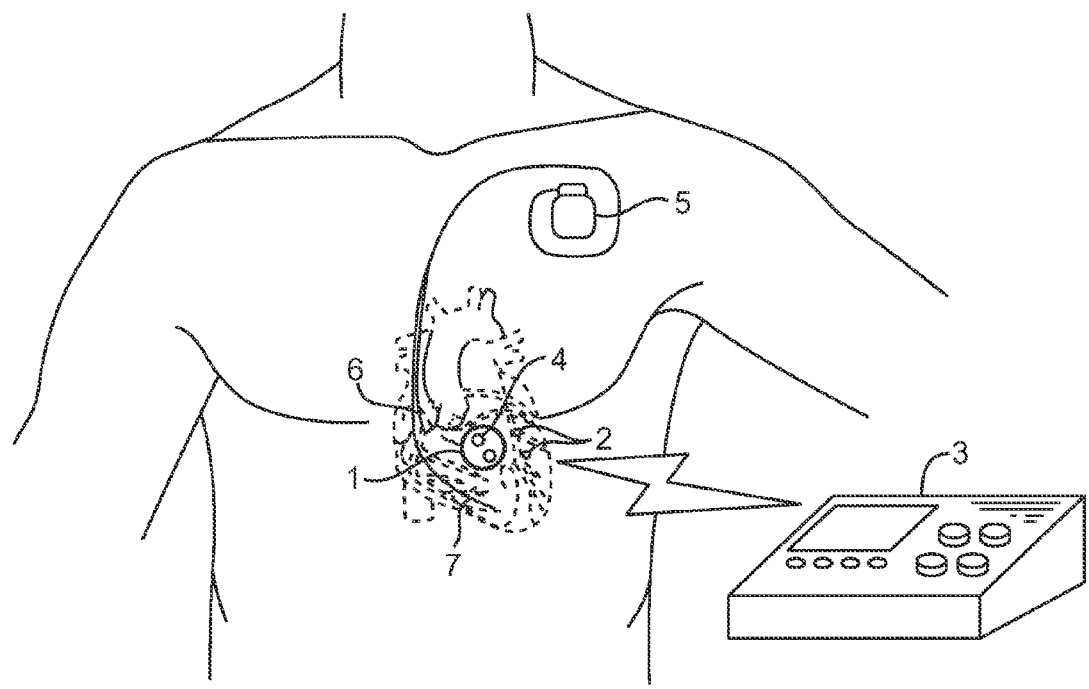
FIGS. 1a and 1b illustrate acoustic cardiac pacing, defibrillation, and cardioversion systems constructed in accordance with the principles of the present invention.

The systems and devices described comprise a controller-transmitter device that will deliver acoustic energy and information to one or more implanted receiver-stimulator device(s) that will convert the acoustic energy to electrical energy of a form that can be used to electrically pace the heart. The acoustic energy can be applied with ultrasound as a single burst or as multiple bursts with appropriate selection of the following parameters:

| Parameter | Value Range |
| --- | --- |
| Ultrasound frequency | 20 kHz-10 MHz |
| Burst Length (#cycles) | 2-10,000 |
| Stimulation Pulse Duration | 0.1 µS-10 mS |
| Duty Cycle | 0.01-0.2% |
| Mechanical Index | ≦1.9 |

The controller-transmitter device would contain an ultrasound transducer or transducers of appropriate size(s) and aperture(s) to generate sufficient acoustic power and signal information to achieve the desired stimulation at the location of an implanted receiver-stimulator device. Additionally, multiple implanted receiver-stimulator devices may be placed within the region insonified by the controller-transmitter device. Multiple receiver-stimulator implants may function simultaneously, however it is possible for multiple devices to function independently, either by responding only to a specific transmitted frequency, or through the use of a selective modulation technique such as amplitude modulation, frequency modulation, pulse width modulation, or through encoding techniques including time-division multiplexing. Such a pacemaker system comprising a controller-transmitter and at least one receiver-stimulator would preferably operate at an ultrasound frequency between 20 kHz and 10 MHz, and more preferably operate at a frequency between 100 kHz and 1 MHz, and most preferably operate at a frequency between 200 kHz and 500 kHz.

The signal information generated by the controller-transmitter will most often comprise pulse width and pulse amplitude information used by the receiver-stimulator to construct a corresponding electrical output. Alternatively, the signal information may comprise address information (identifying a particular receiver-stimulator device or group of devices to trigger), triggering information to initiate output (turn on or off) the receiver-stimulator device(s), delay information to control when the receiver-stimulator device(s) initiate output, the level or other characteristics of the electrical power to be delivered, and the like. The receiver-stimulator device(s) will usually have circuitry to permit decoding of the signal information (which will usually be encoded in the power transmission), and additional circuitry such as a digital gate which can turn on and off the electrical output, timer circuitry to permit a delay in turning on or off the electrical output, and the like.

The controller-transmitter device containing the transmitting transducer would be implanted typically just beneath the skin in the subcutaneous space but could also be placed beneath the pectoral muscles.

The controller-transmitter device would typically include sensors such as electrodes for detecting the patient's electrogram and/or pacing signals (pacing artifacts) from other devices, and in certain embodiments additional physiological sensors including but not limited to sensors which would detect the patient's motion, blood pressure, temperature, respiration, and/or heart sounds. Circuitry and algorithms for utilizing these signals for control of the pacemaker function would be provided. Such electrodes and other sensors would be preferably disposed on or incorporated into or within the housing of the controller-transmitter device.

The acoustic transmitter function may also be incorporated within a device providing conventional lead-based electrical stimulation, for example in a bi-ventricular pacemaker (CRT) or defibrillator (CRT-D) system wherein a conventional lead/electrode system would provide sensing from and stimulus to the right atrium and ventricle, and the receiver-stimulator would provide synchronized stimulation to the left ventricle.

Examples of leadless cardiac pacemaker systems are illustrated in FIGS. 1 through 5 and 8 through 10.

FIG. 1a illustrates a "slave" configuration for biventricular pacing in conjunction with a conventional implanted dual chamber pacemaker. In this example a controller-transmitter device 1 containing circuitry to provide pacing control and ultrasound transmission, plus means to communicate with an outside programmer 3 is implanted beneath the skin, and generally over the heart. An ultrasound signal is transmitted by this device through intervening tissue to the receiver-stimulator device 2, shown implanted in the left ventricle, containing means to receive this acoustic energy and convert it into an electrical pulse which may then be applied to the attached electrodes. In this example a conventional dual chamber (DDD) pacemaker 5 utilizing both a conventional right atrial lead 6 and conventional right ventricular lead 7 is also shown implanted. Controller-transmitter 1 incorporates sensing electrodes 4 and appropriate circuitry and algorithms (not shown) that allow detection of the patient's electrogram and/or the detection of pacing signal artifacts generated by conventional pacemaker 5, providing information whereby the control circuitry can at the proper time initiate the acoustic transmission which will result in left ventricular pacing.

Figure 1B:
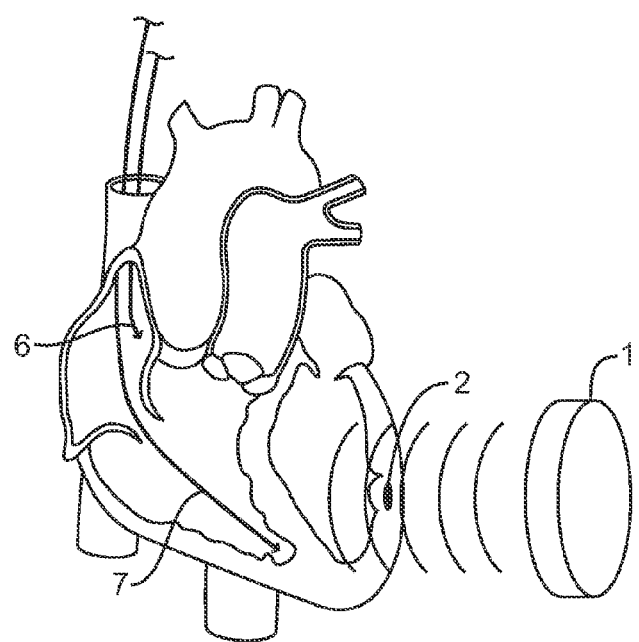

FIG. 1b is a cross-sectional view of the heart in the previous example, showing a single receiver-stimulator device 2 implanted into the left ventricular myocardium, receiving acoustic energy from controller-transmitter 1. Conventional leads 6 and 7 from pacemaker 5 (not shown) are placed in the right atrium and right ventricle, respectively. Optionally (not shown), the receiver-stimulator device 2 could be incorporated into a vascular stent deployed into a coronary vein or artery on the epicardial surface of the left ventricle.

Figure 2A:
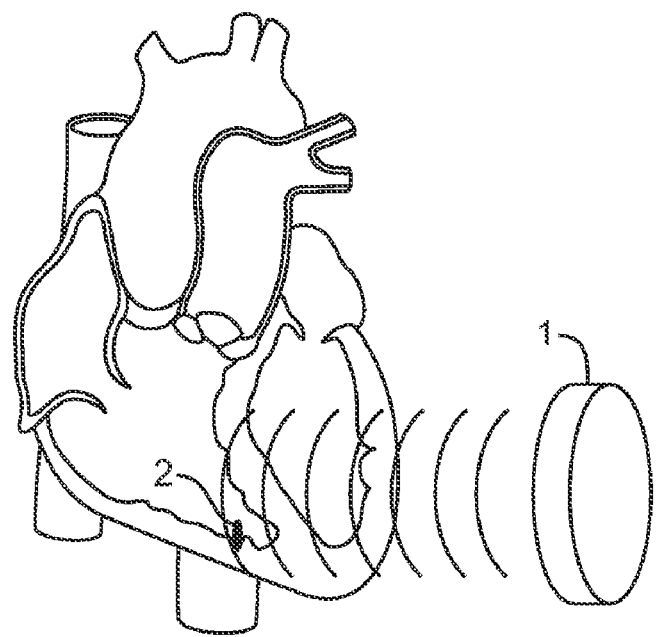
FIGS. 2a and 2b illustrate different combinations of stand alone acoustic cardiac pacemakers constructed in accordance with the principles of the present invention.

FIG. 2 depicts various combinations of stand alone leadless cardiac pacemakers. FIG. 2*a* is a cross-sectional view of the heart showing a single receiver-stimulator 2 implanted into the right ventricle, receiving acoustic energy from controller-transmitter 1. Such an embodiment matches the function of a single chamber (VVI) type pacemaker. Receiver-stimulator 2 could also be implanted into the left ventricle (not shown) to function as a VVI pacemaker. In another adaptation of this example (not shown), a single receiver-stimulator could be implanted into the right atrium to create a single chamber (AAI) type of pacemaker.

Figure 2B:
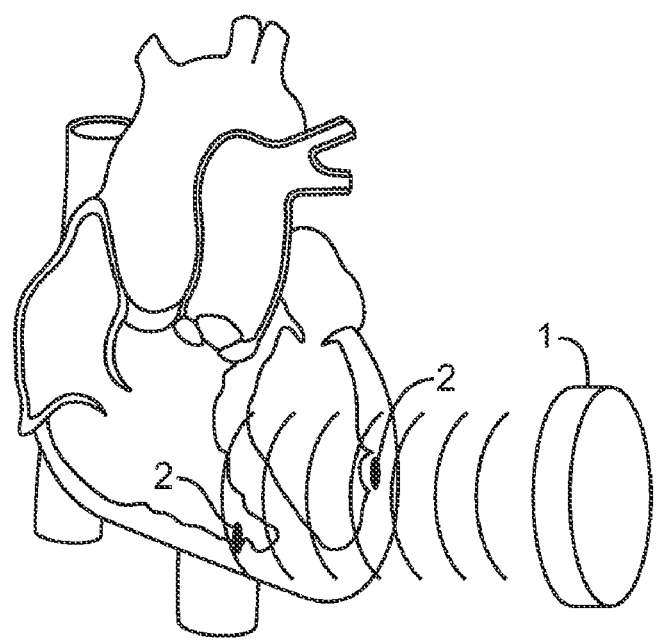

FIG. 2*b* shows a further adaptation wherein two receiver-stimulator devices 2 are implanted to achieve a leadless bi-ventricular pacemaker configuration. The first receiver-stimulator 2 is shown attached to the right ventricular apex with the second being attached to the left ventricular free wall. Both receiver-stimulator devices 2 receive acoustic energy from controller-transmitter 1, either simultaneously or selectively through methods that may include amplitude modulation, frequency modulation, time-division modulation, or other modulation or encoding of the acoustic waveform. In another adaptation (not shown) one of the receiver-stimulator devices could be implanted within the right atrium rather than the left or right ventricle to result in a dual chamber (DDD) type of pacemaker. In a further adaptation (not shown), three receiver stimulator devices could be implanted, into the right atrium, right ventricle, and left ventricle and activated either simultaneously or sequentially through the previously described methods.

A leadless cardiac pacemaker system is shown in more detail in the block diagram of FIGS. 3*a* and 3*b*. In FIG. 3*a* the controller-transmitter device 1 is comprised of: a battery 10 which is optionally a rechargeable battery; multiple electrodes and possibly other sensors including motion sensors 11 which may be in direct contact with tissue to detect the patient's electrocardiogram, pacing signals from other conventional pacemakers, and other physiological parameters possibly including patient activity; these being connected to signal processing circuitry 12; a communications module 13 whose function is to provide a data path, for example by RF communication, to and from an external unit 3 to allow the physician to set device parameters and to acquire diagnostic information about the patient and/or the device; a control and timing module 14 which stores such setup parameter and diagnostic information and uses this information in conjunction with the acquired physiological data to generate the required control signals for the ultrasound amplifier 15 which in turn applies electrical energy to the ultrasound transducer 16 which in turn produces the desired acoustic beam. The controller-transmitter device 1 is encased in a hermetically sealed case 17 constructed of a biologically compatible material, typical of currently existing pacemaker or ICD devices.

Referring to FIG. 3*b*, the receiver-stimulator device 2, implanted in the path of the acoustic beam at the location where electrical stimulation is desired, contains an ultrasound transducer 20 which intercepts a portion of the transmitted acoustic energy and converts it into an alternating electrical signal representing the alternating nature of the applied ultrasound pressure wave. This electrical signal is applied to an electrical circuit 21 which may be one of a type commonly known as an envelope detector, and which may have one of many known circuit configurations, producing a voltage pulse with amplitude proportional to the amplitude of the transmitted ultrasound burst and with a pulse length generally equal to the length of the transmitted burst. The circuit 21 may also be of different configurations and function, for example to provide a fixed delay between the reception of the acoustic energy and the output of the pacing pulse, or to provide output signals having characteristics other than a single pulse. This signal is applied then to electrodes 22 which may be incorporated onto the outer surface of the device, and thus in direct contact with the tissue which is to be stimulated. The receiver-stimulator device 2 is also enclosed within a hermetically sealed case 23 of biologically compatible material.

Figure 4:
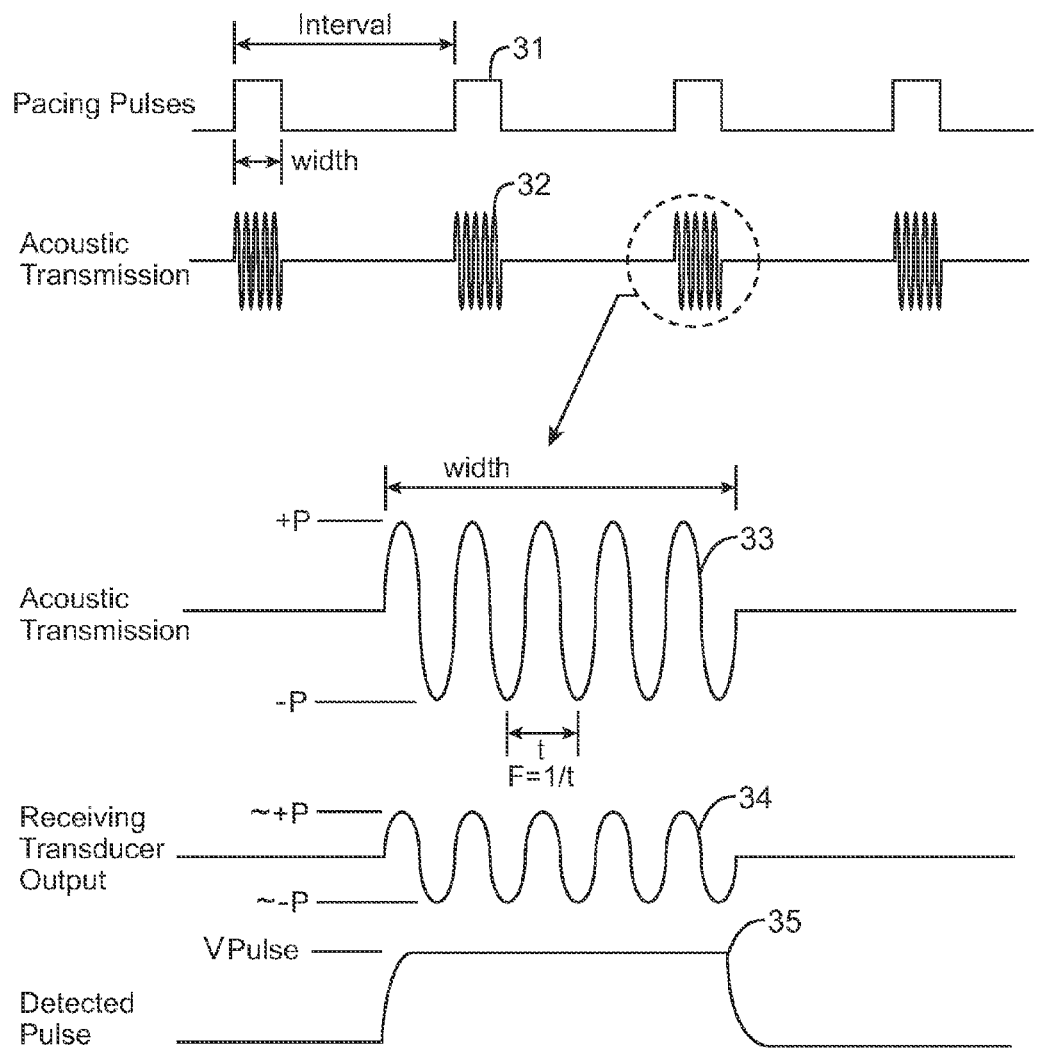
FIG. 4 illustrates representative acoustic and electrical signals useful in the systems and methods of the present invention.

Referring also to previously described FIGS. 3*a* and 3*b*, FIG. 4 provides detail representing example acoustic and electrical signals of the present system. FIG. 4 first depicts a train of pacing pulses 31 which have the desired width and are repeated at a desired interval. The controller-transmitter device 1 produces one or multiple acoustic transmissions 32, at the desired pacing pulse width and repeated at the desired pacing pulse interval, which are emitted from the ultrasound transducer 16. Below waveform 32 is shown an enlargement 33 of a single acoustic burst. This burst again has a desired width, a desired oscillation frequency $F=1/t$, and also a desired acoustic pressure indicated by the peak positive pressure P+ and peak negative pressure P−. The acoustic pressure wave, when striking the receiving transducer 20 of the receiver-stimulator device 2 generates an electrical signal 34 having frequency and burst length matching that of the transmitted waveform 33 and amplitude proportional to the transmitted acoustic pressure (~P+/P−). This electrical waveform is then rectified and filtered by the circuit 21 producing the desired pulse 35 with length equal to the burst length of the transmitted waveform 33 and amplitude ($V_{PULSE}$) proportional to the amplitude of the electrical signal 34. Thus, it can be seen in this example that it is possible to vary the pacing rate by varying the time between ultrasound bursts, to vary the duration of any one pacing pulse by varying the duration of the ultrasound burst, and to vary the amplitude of the pacing pulse by varying the amplitude of the ultrasound waveform.

In practice, the amount of energy (amplitude) received by the implanted receiver-stimulator device will vary due to ultrasound attenuation caused by loss in the intervening tissue and bone, due to spatial location of the receiver-stimulator device with respect to the transmitted ultrasound beam as such a beam is typically non-uniform from edge-to-edge, and possibly due to orientation (rotation) of the receiver-stimulator device with respect to the controller-transmitter device. Such variation would affect the amplitude of the stimulation output pulse for any given ultrasound transmit power (acoustic pressure amplitude). This limitation can be overcome by adjusting the ultrasound transmit power until stimulation is consistent, a technique similar to that used currently to determine pacing thresholds at the time of pacemaker implantation; additionally this can be adjusted automatically by algorithms within the controller-transmitter device that periodically determine stimulation thresholds and adjust power transmission accordingly to compensate for any change in the system including relative movement between the transmitting and receiving devices. This limitation may also be mitigated by design of the transducer incorporated into the receiver-stimulator device to be omni-directional in its reception capability, for example by using a spherical transducer or by using multiple transducers disposed at appropriate angles to reduce or eliminate the directional sensitivity of the device.

Figure 5A:
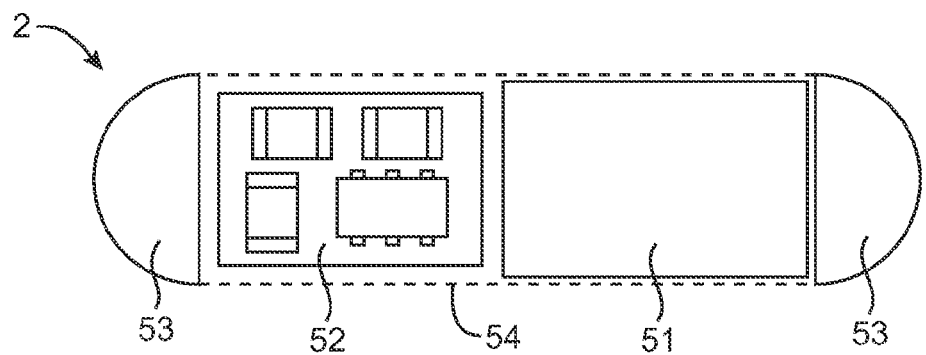
FIGS. 5a-5c illustrate two embodiments of a small implantable receiver-stimulator according to the principles of the present invention.
Figure 5B:
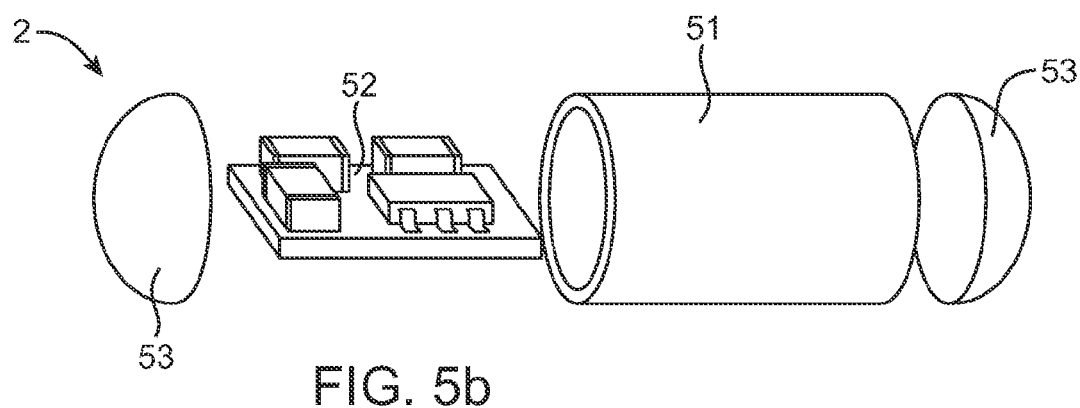
Figure 5C:
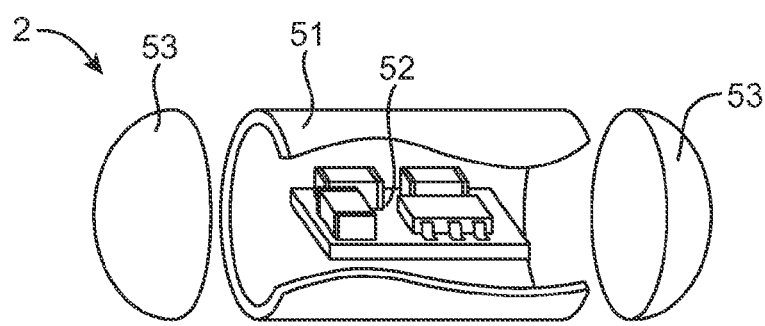

FIGS. 5*a* through 5*c* illustrate two embodiments of a small implantable receiver-stimulator of a cylindrical profile, suitable for placement by catheter, stylet, or other means adapted for its delivery. FIG. 5a shows in plan view and 5b in perspective view such a receiver-stimulator 2 having a hollow, cylindrical ultrasound transducer 51, a circuit assembly 52 comprising at least a detector circuit and possibly other circuits and functions, and two electrodes 53 at either end of the assembly. The transducer 51 would be of a rigid piezoelectric material, typically a piezoelectric ceramic or single crystal piezoelectric element with electrodes deposited on the opposing surfaces of the cylinder. Alternately (not shown), the transducer 51 could be fabricated from multiple smaller cylindrical sections connected either in series, in parallel, or a combination thereof. Alternately (not shown), the transducer 51 might be a composite fabrication containing multiple elements disposed about the cylindrical body. The transducer and circuit would be enclosed in an electrically insulating but acoustically transparent biocompatible housing 54. The circuit assembly 52 may be fabricated using known surface-mount or hybrid assembly techniques, upon either a fiberglass or ceramic substrate. Electrodes 53 would be fabricated of material commonly used in implanted electrodes, such as platinum, platinum-iridium, or preferably of a steroid-eluting design. Necessary electrical wiring between the transducer, circuit board, and electrodes is not shown in these drawings. The receiver-stimulator of this design would also incorporate means such as helical coils, barbs, tines, clips, and the like (not shown) to affix the device within, or onto, or in contact with, the myocardium in the desired location. Such fixation means may vary depending on the intended implant location and delivery method. Typical dimensions of such a device would be 1.5 cm in length and 3.0 mm in diameter, and preferably less than 1.0 cm in length and 2.0 mm in diameter, exclusive of fixation features.

As shown in FIG. 5c, by using hybrid circuit techniques it may be possible to further miniaturize the circuit assembly 52 such that it would fit inside the hollow interior of the transducer 51. This would have the benefit of substantially reducing the length of the finished device.

Figure 8:
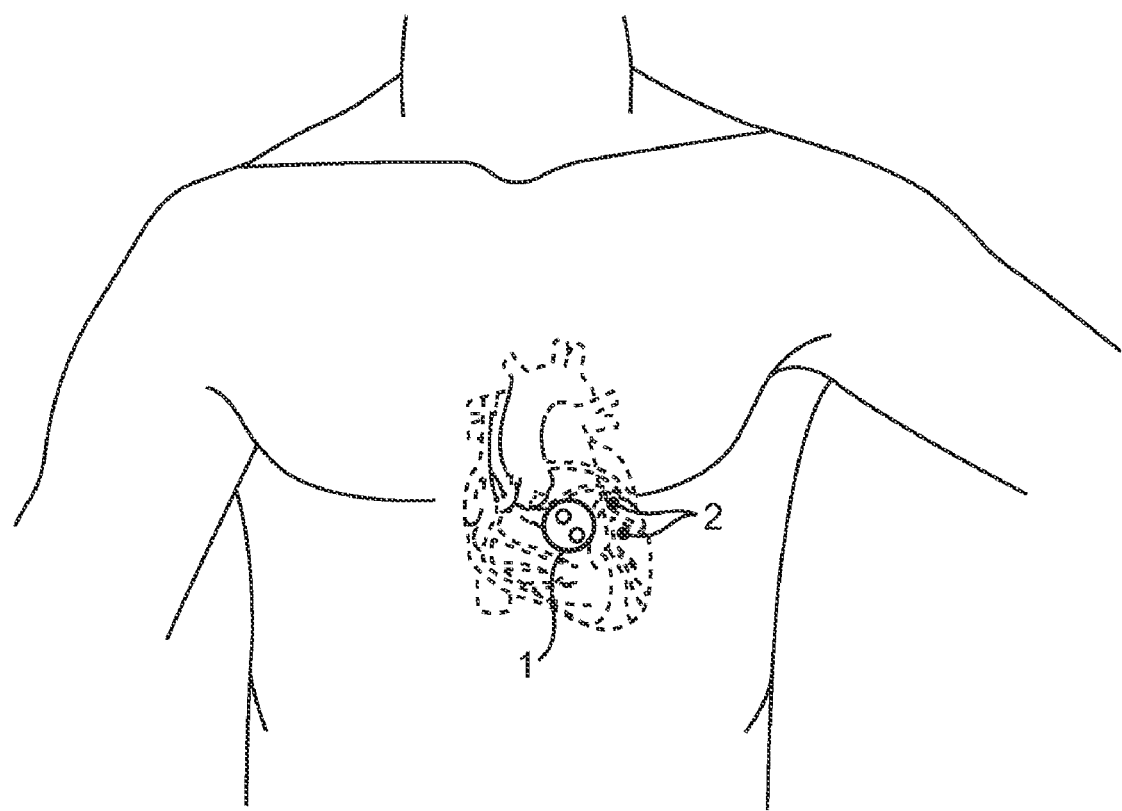
FIG. 8 illustrates a stand alone acoustic cardiac pacemaker system constructed in accordance with the principles of the present invention.

As depicted in FIG. 8, for the treatment of tachycardias, one or more receiver-stimulator elements 2 would be implanted within the heart. In this illustration receiver-stimulators are implanted in the left ventricle. For ATP, the device(s) would be implanted at sites which would be optimal for interacting with a tachycardia episode. Using VT as an example, standard electrical activation sequence mapping performed during VT can identify the location and pathway of the VT reentry circuit within the left ventricle as well as areas of slow conduction. Using this testing, a specific site or sites can be identified that would be most responsive to ATP algorithms. A single receiver-stimulator may be sufficient to treat the rhythm disorder however using multiple receiver-stimulators increases the ability to pace at different sites and perhaps at different times to effectively block the conduction of the arrhythmia in order to terminate the condition. The use of multiple receiver-stimulators would generally be used for the suppression or treatment of atrial fibrillation and ventricular fibrillation. The controller-transmitter 1 would be implanted in a subcutaneous location and situated to insonify the receiver-stimulators. Pacing sequences would originate in the controller-transmitter based on ATP algorithms intended to terminate the tachycardia. The controller-transmitter may contain one or more algorithms that deliver pacing therapy in attempts to terminate the arrhythmia. In its simplest embodiment, no other components illustrated in FIG. 8 are necessary for treating tachycardia.

The leadless cardiac pacemaker system shown in FIGS. 3a and 3b may be adapted for treating tachycardias as follows.

The controller-transmitter device 1 is comprised of a battery 10 which is optionally a rechargeable battery; multiple electrodes and/or other sensors 11 which may be in direct contact with tissue to detect the patient's electrocardiogram, pacing signals from other conventional pacemakers, and/or other physiological parameters possibly including patient activity; these being connected to signal conditioning/processing circuitry 12; a communications module 13 whose function is to provide a data path, for example by RF communication, to and from an external programming and/or communicating unit 3 to allow the physician to set device parameters and to acquire diagnostic information about the patient and/or the device; an arrhythmia detection, control, and timing module 14 which processes electrogram or other cardiac information to determine the presence or absence of a tachycardia, stores setup parameters, stores diagnostic information and uses this information in conjunction with the acquired physiological data to generate the required control signals for the ultrasound amplifier 15 which in turn applies electrical energy to the ultrasound transducer 16 which in turn produces the desired acoustic beam. By varying the timing and control of the output, antitachycardia prevention and termination pacing algorithms are delivered from the controller-transmitter. The controller-transmitter device 1 is preferably encased in a hermetically sealed case 17 constructed of a biologically compatible material, typical of currently existing pacemaker or ICD devices.

Figure 6:
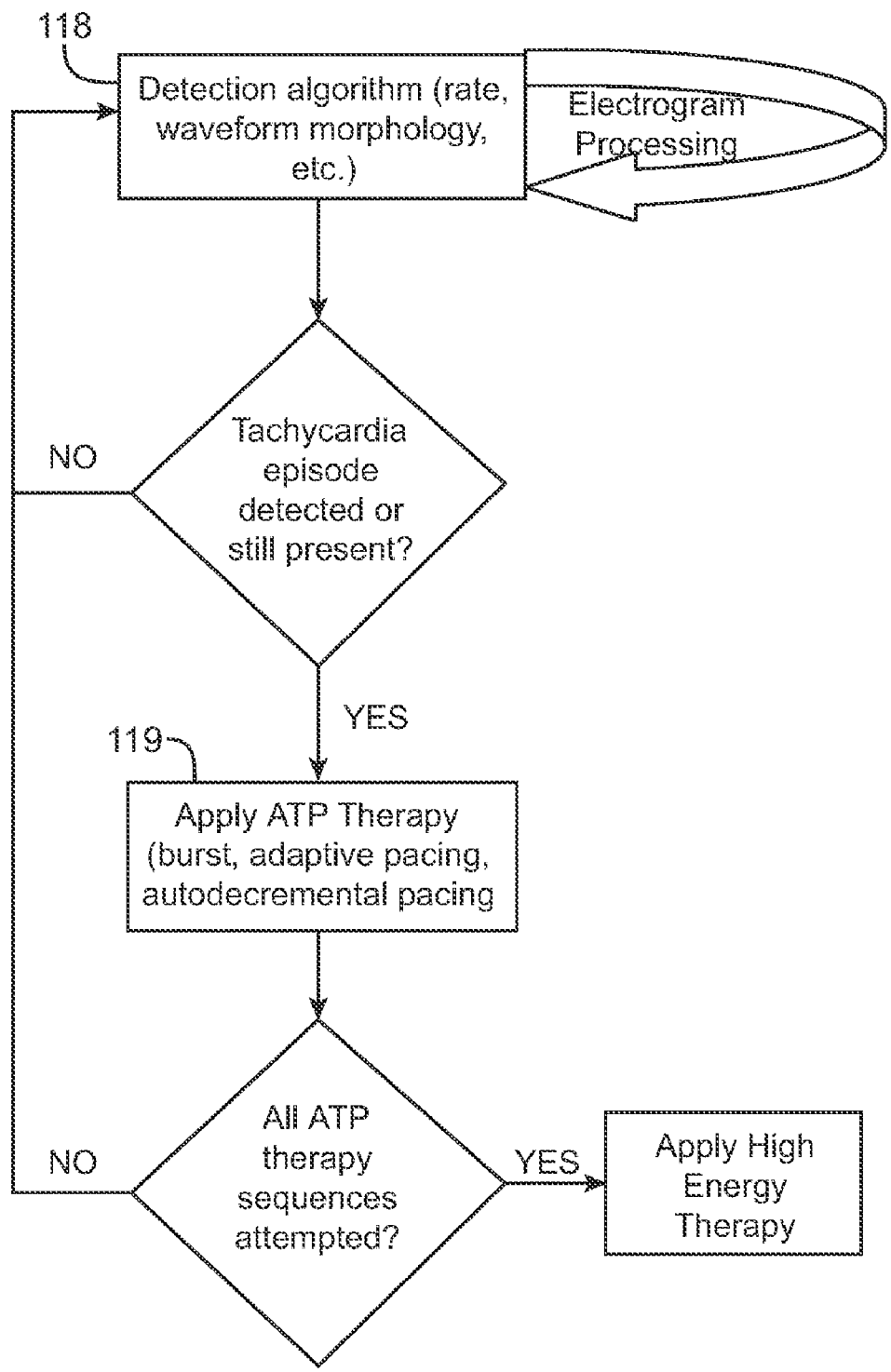
FIG. 6 is a block diagram illustrating methods for treating tachyarrhythmia according to the principles of the present invention.

A simple block diagram of logic used for arrhythmia detection and antitachycardia pacing therapy control is depicted in FIG. 6. The arrhythmia detection algorithm 118 would use known techniques and data processed from the electrogram or other cardiac information, for example, rate determination, rate variability, waveform morphology, time/signal excursions from baseline etc., to determine whether a tachycardia episode is present. The therapy delivery algorithm 119 would use known techniques for therapy algorithms for example burst pacing, rate adaptive pacing, overdrive suppression pacing, autodecremental pacing, premature stimuli, etc. to terminate the arrhythmia. One or more detection schemes or pacing therapies may be present in the controller 14 and adjusted based on programming communication to the controller 14.

Examples of leadless cardiac pacemaker systems suitable for delivery of ATP are illustrated in FIG. 1a with systems specifically adapted for ATP and illustrated in FIGS. 7a to 7c and 8.

FIG. 1a illustrates a "slave" configuration for leadless ATP used in conjunction with a lead-based pacemaker, cardioverter, and/or defibrillator device. Similar to the previous description for FIG. 1a, the controller-transmitter would detect pacing signals generated by the co-implanted pacemaker or defibrillator and initiate an acoustic transmission to activate the receiver-stimulator with each ventricular pacing signal detected. The algorithm logic for the detection of the arrhythmia and the delivery of ATP would be a component of the pacemaker or defibrillator.

Figure 7A:
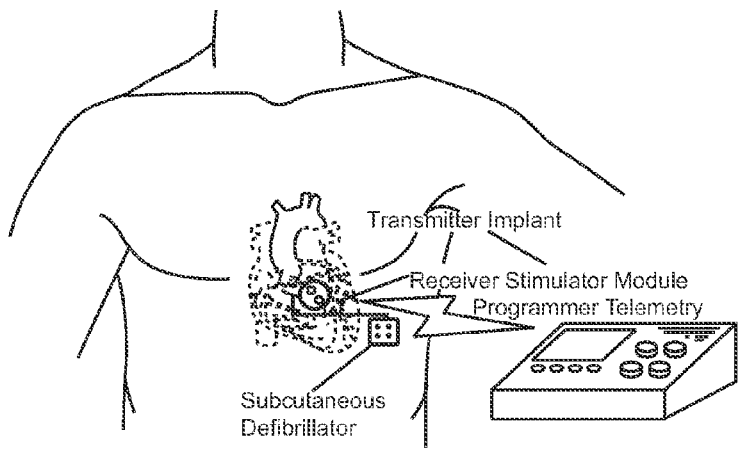
FIGS. 7a-7c illustrate systems according to the present invention for treating tachycardias alone or in combination with pacing and defibrillator systems.
Figure 7B:
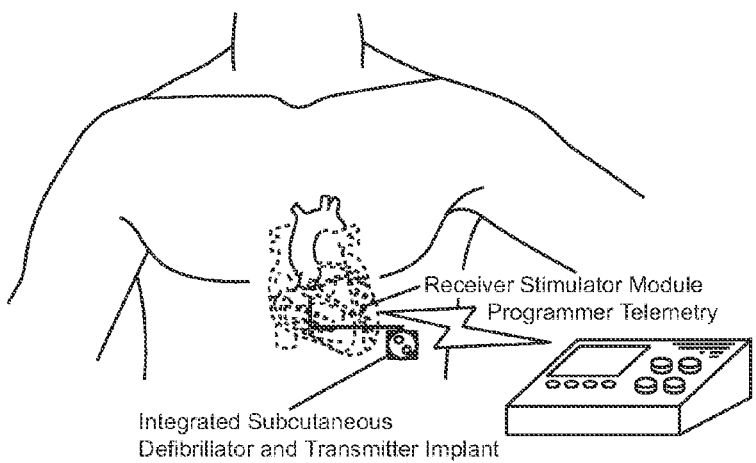
Figure 7C:
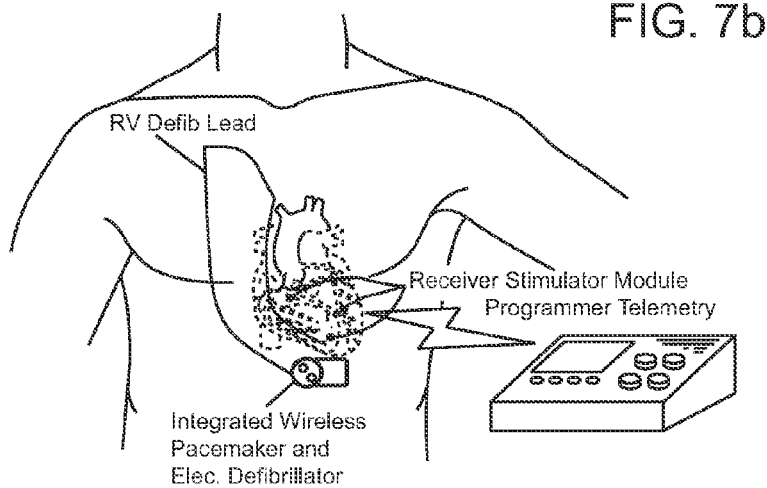

FIG. 7a illustrates a leadless ATP device used in conjunction with a leadless cardioverter or defibrillator device. FIG. 7b illustrates an integrated leadless device using acoustic transmission to receiver-stimulators for ATP and using high energy subcutaneous electrodes for cardioversion and/or defibrillation. FIG. 7c illustrates an integrated lead-based defibrillator device incorporating a leadless pacing system that uses acoustic transmission to receiver-stimulators for ATP and uses a high energy coil electrode on a lead in the RV for cardioversion and/or defibrillation. FIG. 8 represents the a stand alone configuration for an ATP device as described above.

Figure 9A:
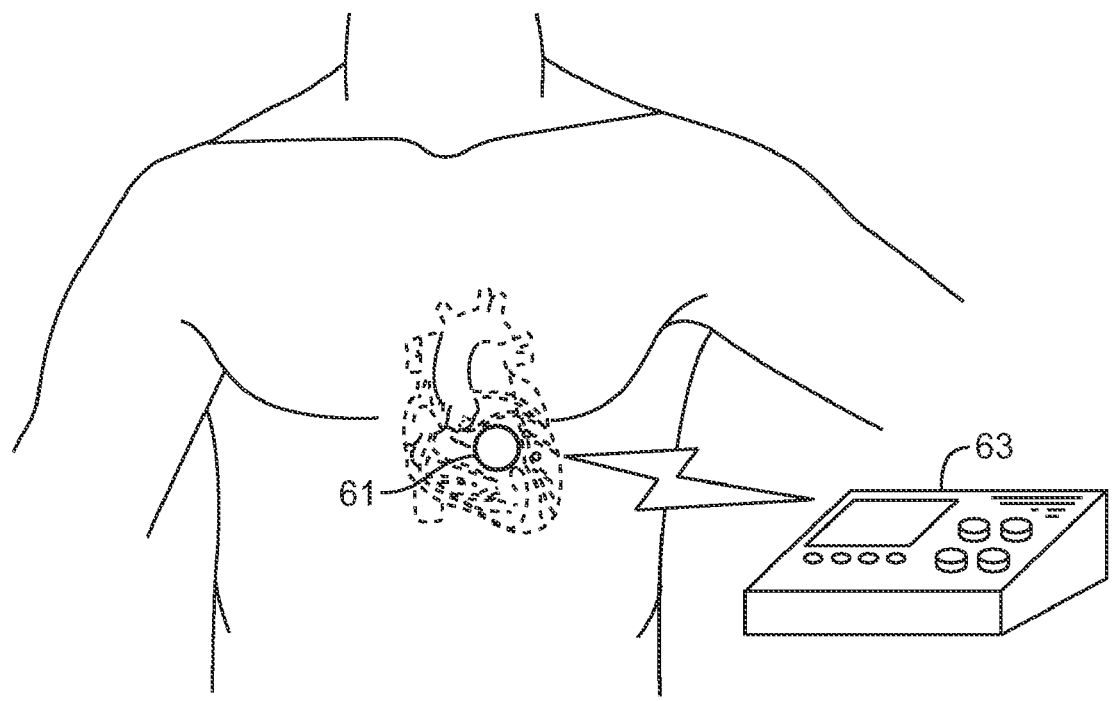
FIGS. 9a and 9b illustrate an implanted cardiac pacemaker system in accordance with the principles of the present invention.
Figure 9B:
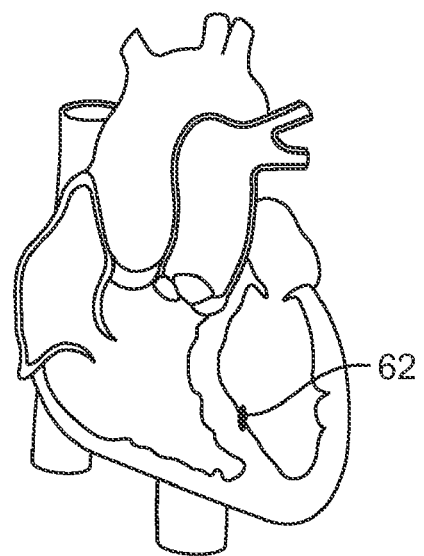

In FIGS. 9a and 9b, an implanted leadless single chamber cardiac pacemaker system of the present invention is illustrated in an exemplary embodiment as a "standalone" cardiac pacemaker system. As can be appreciated this standalone system can be adapted to a dual chamber system (not shown). FIG. 9a, depicting the controller-transmitter device 61 containing circuitry to provide pacing control and acoustic transmission, is implanted just beneath the skin, and generally over the heart. The controller-transmitter includes wireless circuitry to communicate with an outside programmer 63. Acoustic energy is transmitted by controller-transmitter device 61 through intervening tissue to a receiver-stimulator device 62 containing transducers and circuitry to receive the acoustic energy and convert it into electrical pulse(s) which may then be applied to tissue through the attached electrodes. In FIG. 9b, receiver-stimulator device 62 is shown attached to the left ventricular septum. The receiver-stimulator device 62 is shown as a small cylindrical or button-shaped device that would be affixed to the heart muscle with an attaching screw-in helix, similar to conventional pacing lead wires fixed to the heart as in current pacemaker systems, or other method (for example with barbs, tines, clips, sutures or the like) of attaching permanently implanted devices to the heart.

FIGS. 10a, 10b, and 10c, illustrate a testing and positioning system for a leadless cardiac pacemaker system as in any of the above embodiments, for example as depicted in FIGS. 9a and 9b. The testing and positioning system is used to evaluate various positions for implant of the receiver-stimulator 62 in the heart and for implant of the controller-transmitter 61 in the chest. Testing is performed for example, to determine appropriate levels of transmitted and received acoustic energy and subsequent electrical output energy from the receiver-stimulator required to capture/pace cardiac tissue. Knowledge of the amplitude of transmitted energy would be needed to optimize positioning of the implanted receiver-stimulator and implanted controller-transmitter, for example to efficiently utilize battery power. Further, testing may be performed to identify areas on the chest that would ensure acoustic reception by the receiver-stimulators without restriction from chest contours or interference from the lungs or other internal tissue structures. This is referred to as an acoustic window or a targeting window. Still further, testing may be performed to assess patient response, for example electrophysiologic or contraction responses based on capture/pacing at a site. The observed patient response would be evidence of pacing on the electrocardiogram or other measures of heart function such as blood pressure or contractility.

An external controller-transmitter system 64 will generally be used for positioning and testing, which will typically be able to be reused on different patients. Controller-transmitter device 64 includes external acoustic transmitter 65 and manual or other controller 66, typically connected by cable 67, however it can be appreciated that the transmitter 65 could be integrated into controller 66 and the integrated device used as an external transmitter. Transmitter 65 is typically placed overlying the skin surface, with acoustic transmission gel used for coupling. Also used in the testing and positioning system, as shown in FIGS. 10b and 10c, is a receiver-stimulator device 62, which may be positioned in any endocardial location using venous or arterial transvascular access to the heart with a catheter-based delivery system 68. Prior to permanent insertion (implant) of the receiver-stimulator 62 into the tissue, device 62 will be temporarily mounted onto delivery system 68. Alternatively (not shown) a similar catheter-based device containing a receiver-stimulator element that is permanently affixed on the device may be used for site selection by positioning and testing sites anywhere on the endocardium or in the myocardium. FIG. 10c shows further detail of a typical delivery system 68 for receiver-stimulator device 62.

Ideally, prior to permanent insertion/deployment from the delivery system, the pacing electrodes on the receiver-stimulator would be accessible via connecting wires that run the length of the delivery system (not shown). This example of a delivery system 68 comprises a catheter 69 onto which receiver-stimulator device 62 is affixed to the distal end. Catheter 69 with receiver-stimulator 62 is inserted into a steerable guiding sheath 70. Other possible variations of delivery system 68 may be utilized, including a catheter 69 which is steerable and would be used in place of a steerable guiding sheath. Delivery system 68 enables manipulation and repositioning of receiver-stimulator 62 within the vasculature or heart chambers. In this example, the delivery system 68 would position the receiver-stimulator 62 and test the cardiac site, then the delivery system 68 would be moved to another location and that site tested. Once an optimal position is found, implantable device 62 would be deployed from catheter 69, by first being implanted at the tested location by a fixation means and then being released from catheter 69 by a mechanical means. In an alternative case, the testing catheter 69 with permanently affixed device 62 is removed from steerable guiding sheath 70, and a second catheter 69 having a releasable implantable device 62 is introduced to the location by catheter 69 through steerable guiding sheath 70, or a separate delivery system 68 adapted to implant device 62.

A first method may be used in situations in which the ideal location for the controller-transmitter 61 is known or limited due to anatomic constraints, but more than one location for the receiver-stimulator 62 is possible. Typically, the external controller-transmitter 64 will be used for testing purposes with acoustic transmitter 65 positioned on the skin surface overlying its ideal or otherwise predetermined location. Transmission gel will be used as coupling agent between the external acoustic transmitter 65 and the skin. Alternatively, (shown in FIG. 9a), an implantable controller-transmitter device 61 may be surgically placed under the skin in the final implant location and controlled with an external programmer. The receiver-stimulator device 62 will be placed in a first test position by maneuvering delivery system 68. Acoustic energy will then be transmitted/delivered using external controller 66 or alternatively the implantable controller-transmitter 61 under direction of programmer 63 to evaluate efficacy at that location. If the results are not satisfactory or if there is a desire to evaluate additional positions, the receiver-stimulator device 62 will be moved to a new site with the aid of delivery system 68, acoustic energy will be transmitted/delivered, and efficacy at this site will be tested. This sequence can be repeated until the desired location for implantation of the receiver-stimulator device 62 is identified. The receiver-stimulator device 62 will then be delivered or deployed to that location and the delivery system 68 removed. If an external controller-transmitter 64 was used, but an implanted device 61 is intended to be implanted, the location of the externally applied controller-transmitter will be noted and an incision and dissection will be performed, as known in the art, for implantation of device 61.

One example (in addition to cardiac pacing) in which this method may be utilized is epilepsy, where the controller-transmitter location will be known because it will be confined to a site near the craniotomy. In this case, a multiplicity of receiver-stimulators will typically be implanted into the brain tissue. The controller-transmitter typically would be positioned outside of the brain tissue either within the craniotomy opening or outside the cranium under the skin. The positioning and testing of the placement of the receiver-stimulators will be based upon the effects of the electrical stimulation on electroencephagraphy mapping. Another example in which this method may be utilized is Parkinson's disease, wherein, similar to the treatment of epilepsy, the controller-transmitter will be confined to a site near the craniotomy and a multiplicity of receiver-stimulators will typically be implanted into brain tissue. In the case of Parkinson's disease, however, the placement of the receiver-stimulators may be based upon the effects of electrical stimulation on patient responses such as reducing tremor.

A second method of optimization may be used in situations in which the implant location for the receiver-stimulator is known, but the ideal location for the controller-transmitter implant may vary. The receiver-stimulator device 62 is first implanted in its ideal location or alternatively held in its ideal location by delivery system 68. The transmitter 65 of the external controller-transmitter device 64 is placed at the first test location on the skin, using transmission gel for coupling. Energy is then transmitted/delivered using external controller 66 to evaluate efficacy at this location. The transmitter 65 can be moved and the testing sequence repeated until the desired position is identified. The implantable controller-transmitter 61 is then implanted at the location identified to be optimal.

One example in which this method may be utilized is in the treatment of bone fractures. In this case, the location of the receiver-stimulator device will be determined by the location of the fracture. Possible locations for the controller-stimulator device can then be tested to optimize transmission of acoustic energy.

A third method of optimization may be used in situations in which the implant location for neither the receiver-stimulator device 62 nor the controller-transmitter device 61 is known. This method utilizes procedures specified above in both the first and second methods. In this situation, after testing the devices at initial locations, the locations of both the devices are changed in alternation in subsequent testing, and this is repeated until the desired, optimal results are obtained. Then, both devices 61 and 62 are implanted.

One example in which this third method may be utilized is a cardiac pacemaker capable of multisite pacing (such as a dual chamber pacemaker or bi-ventricular pacing for heart failure). There are many potential locations to implant the receiver-stimulator devices, but some locations will provide better physiological benefit to the patient. The ideal location for the controller-transmitter device will be the site where the most acoustic energy can be delivered to the multiple receiver-stimulator devices, but there may be some constraints on location imposed by the chest contour and the intervening lungs. Therefore, optimization of the implant locations for the devices may require testing at different sites for each device. The observed patient response would be evidence of pacing on the electrocardiogram or other measures of heart function such as blood pressure or contractility.

These methods can be beneficial to all the applications of the implantable leadless stimulator system and are not meant to be limited to the examples provided herein.

What is claimed is:

1. A method for stimulating cardiac muscle, said method comprising:
   implanting a receiver-stimulator at a cardiac stimulation site, wherein the receiver-stimulator is present in a sealed case; and
   subcutaneously implanting a controller-transmitter at a location remote from the cardiac stimulation site, wherein the controller-transmitter is present in a sealed case separate from that of the receiver-stimulator and is configured to detect a pacing signal of a separate cardiac pacemaker having leads implanted in a right ventricle or right atrium;
   wherein the controller-transmitter detects the pacing signal of the cardiac pacemaker; and upon detecting the pacing signal, generates acoustic energy which is received by the receiver-stimulator and converted by the receiver-stimulator into cardiac stimulation energy based on both energy and signal information included in the acoustic energy.

2. A method as in claim 1, wherein receiving comprises receiving the energy at at least two different cardiac stimulation sites.

3. A method as in claim 2, wherein the signal information sequentially activates at least two receiver-stimulators to stimulate at least two different cardiac sites sequentially.

4. A method as in claim 2, wherein the signal information simultaneously activates at least two receiver-stimulators to stimulate at least two different cardiac sites simultaneously.

5. A method as in claim 1, wherein the cardiac stimulation energy is delivered to treat a cardiac arrhythmia.

6. A method as in claim 1, wherein the cardiac stimulation energy is delivered to terminate a cardiac arrhythmia.

7. A method as in claim 1, wherein the cardiac stimulation energy is delivered to treat heart failure.

8. The method of claim 1, wherein the cardiac stimulation site is in the left ventricle.

9. A method for stimulating cardiac muscle, said method comprising:
   implanting a receiver-stimulator at a cardiac stimulation site, wherein the receiver-stimulator is present in a sealed case; and
   subcutaneously implanting a controller-transmitter at a location remote from the cardiac stimulation site, wherein the controller-transmitter is present in a sealed case separate from that of the receiver-stimulator and is configured to detect a pacing signal of a separate cardiac pacemaker having leads implanted in a right ventricle or right atrium;
   wherein the controller-transmitter generates acoustic energy which is synchronized with the pacing signal of the cardiac pacemaker; and wherein
   the receiver-stimulator converts the acoustic energy into cardiac stimulation energy based on both energy and signal information included in the acoustic energy.

10. A method as in claim 9, wherein stimulating cardiac muscle provides left ventricular stimulation synchronously with right ventricular pacemaker stimulation.

11. A method as in claim 9, wherein stimulating cardiac muscle provides right ventricular stimulation synchronously with left ventricular pacemaker stimulation.

12. A method as in claim 9, wherein the synchronizing with the pacing signal is achieved by sensing atrial and/or ventricular pacing signal artifacts on an electrogram signal.

13. A method as in claim 9, wherein the synchronizing with the pacing signal is achieved by a direct connection from the controller-transmitter to a pacing output of the separate cardiac pacemaker.

14. A method as in claim 9, wherein the synchronizing with the pacing signal is achieved by a direct communication connection to the co-implanted cardiac pacemaker.

15. A method as in claim 9, further comprising detecting intrinsic or non-intrinsic cardiac beats from an electrogram signal.

16. A method as in claim 15, wherein the synchronizing is further based on a combination of the detected intrinsic cardiac beats or the non-intrinsic cardiac beats with the pacing signals from the electrogram signal.

17. The method of claim 9, wherein the cardiac stimulation site is in the left ventricle.

* * * * *

UNITED STATES PATENT AND TRADEMARK OFFICE
CERTIFICATE OF CORRECTION

PATENT NO. : 7,610,092 B2 Page 1 of 1
APPLICATION NO. : 11/315023
DATED : October 27, 2009
INVENTOR(S) : Cowan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 561 days.

Signed and Sealed this

Twelfth Day of October, 2010

David J. Kappos
*Director of the United States Patent and Trademark Office*